United States Patent
Kim et al.

(10) Patent No.: US 9,585,730 B2
(45) Date of Patent: Mar. 7, 2017

(54) DENTAL IMPLANT INSERTION SET AND MANUFACTURING METHOD THEREOF

(71) Applicant: DIO Corporation, Busan (KR)

(72) Inventors: Jin Chul Kim, Yangsan-si (KR); Byung Ho Choi, Wonju-si (KR); Seung Mi Jung, Wonju-si (KR)

(73) Assignee: DIO CORPORATION, Busan (KR)

( * ) Notice: Subject to any disclaimer, the term of this patent is extended or adjusted under 35 U.S.C. 154(b) by 91 days.

(21) Appl. No.: 14/656,769

(22) Filed: Mar. 13, 2015

(65) Prior Publication Data
US 2015/0265372 A1  Sep. 24, 2015

(30) Foreign Application Priority Data

Mar. 18, 2014  (KR) .......... 10-2014-0031435
May 9, 2014  (KR) .......... 10-2014-0055822

(51) Int. Cl.
| | |
|---|---|
| *A61C 13/225* | (2006.01) |
| *A61C 1/08* | (2006.01) |
| *A61C 8/00* | (2006.01) |
| *A61C 9/00* | (2006.01) |
| *A61B 6/14* | (2006.01) |
| *A61C 13/08* | (2006.01) |
| *G06T 7/00* | (2006.01) |

(52) U.S. Cl.
CPC ............... *A61C 1/084* (2013.01); *A61B 6/14* (2013.01); *A61C 1/082* (2013.01); *A61C 8/00* (2013.01); *A61C 8/006* (2013.01); *A61C 9/004* (2013.01); *A61C 9/0053* (2013.01); *A61C 13/08* (2013.01); *G06T 7/003* (2013.01); *A61C 8/0089* (2013.01); *G06T 2207/30036* (2013.01)

(58) Field of Classification Search
CPC ....... A61C 1/084; A61C 9/004; A61C 9/0053; A61C 1/082; A61C 8/00; A61C 8/006; A61C 8/0089; A61B 90/39
USPC .................... 433/75, 76, 172, 174
See application file for complete search history.

(56) References Cited

U.S. PATENT DOCUMENTS

| | | | |
|---|---|---|---|
| 2009/0011382 A1* | 1/2009 | Bavar ............... | A61C 1/084 433/76 |
| 2013/0337400 A1* | 12/2013 | Yi ................. | A61B 6/14 433/25 |
| 2014/0205969 A1* | 7/2014 | Marlin ............ | A61C 8/0001 433/173 |

* cited by examiner

*Primary Examiner* — Michael Carey
(74) *Attorney, Agent, or Firm* — Paratus Law Group, PLLC

(57) ABSTRACT

Disclosed is a dental implant insertion set including a crown; a fixture which has a hex hole formed therein and of which an insertion angle is set so that the hex hole is aligned corresponding to an arrangement angle of the crown; a guide stent including a stent body formed with a profile set through the three-dimensional procedure guide image to be fixed while covering the periodontal tissue; and an abutment having a hex protrusion formed at a lower portion thereof to be matched with and fixed into the hex hole, such that the crown is aligned and fixed.

9 Claims, 12 Drawing Sheets

DENTAL IMPLANT INSERTION SET AND MANUFACTURING METHOD THEREOF

CROSS-REFERENCE TO RELATED APPLICATION

This application claims the benefit of Korean Application No. 10-2014-31435 which was filed on Mar. 18, 2014 and published on Sep. 30, 2015 with a Korean Publication No. 10-2015-0108535, and which is now pending, and Korean Application No. 10-2014-55822 which was filed on May 9, 2014 and issued as a Korean Patent on Sep. 14, 2015 with a Korean Patent No. 10-1554157, which were hereby incorporated by reference as if fully set forth herein.

BACKGROUND

1. Field of the Invention

The present invention relates to a dental implant insertion set and a manufacturing method thereof, and more particularly, to a dental implant insertion set which guides an insertion position of a fixture and a drilling operation for insertion of the fixture in an implant procedure, while enhancing convenience and accuracy in fixture insertion and crown coupling, and a manufacturing method thereof.

2. Discussion of Related Art

Generally, an implant means a substitute which may replace a human tissue when the original human tissue is lost, and also means a dental implant in which an artificial tooth is implanted. In the dental implant, a fixture formed of titanium having no rejection to human body is implanted in an area of an alveolar bone, from which a tooth comes out, to replace a lost dental root, and then an artificial tooth is fixed thereon to restore a function of the tooth.

FIG. 1 is a flowchart illustrating a conventional implant procedure.

As illustrated in FIG. 1, the conventional implant procedure includes primary processes s1, s2, s3 and s4 in which the fixture is implanted in the alveolar bone, and final processes s5 and s6 in which a crown is finally fixed after a period of time (3 to 6 months) while the fixture is osseointegrated with the alveolar bone.

The primary processes s1, s2, s3 and s4 includes a gum removing operation s1 of opening a part of gum from which the tooth is lost, a multi-stage drilling operation s2 of forming a bore in which the fixture is implanted, a fixture implanting operation s3, and an operation s4 of coupling a provisional crown to the implanted fixture.

Specifically, in the gum removing operation s1, the gum is removed using a tissue punch or the like, and thus the alveolar bone corresponding to a position in which the fixture is implanted is exposed. The bore for fixture implant is formed in the exposed alveolar bone through the multi-stage drilling operation s2.

At this time, the multi-stage drilling operation s2 includes an operation of forming an initial hole, an operation of expanding the hole, an operation of forming a screw thread in the hole, and an operation of removing remaining alveolar bone from the hole.

The fixture is implanted in the bore formed through the multi-stage drilling operation s2 (s3), and the provisional crown is coupled to the implanted fixture (s4), and thus the primary processes are finished.

Here, the fixture which is implanted in the bore serves as a root of an artificial tooth. Therefore, a restoring process in which the alveolar bone is osseointegrated with the fixture is rapidly and stably performed. To provide a stable coupling force between the alveolar bone and the fixture after the osseointegration, it is very important to accurately form the bore in the multi-stage drilling operation s2, and completion in formation of the artificial tooth through the dental implant is influenced by this.

At this time, the provisional crown includes a healing abutment and a cover screw. Here, the healing abutment and the cover screw are inserted into the bore for a period of time while the abutment and the crown are manufactured after the fixture is implanted in the alveolar bone, and prevent foreign substances from being introduced.

After restoration of the alveolar bone for about 3 to 6 months after the provisional crown is coupled to the fixture, the provisional crown is removed and the abutment is coupled (s5). Finally, the crown is coupled to the abutment, and the implant procedure is completed (s6).

Meanwhile, in the above-described processes, it is very difficult for an unskilled operator as well as a skilled operator to form the bore to a precise depth and in a precise direction at the position in which the fixture is implanted. Therefore, the drilling operation forming the bore is performed using a procedure guide tool called as a 'stent'.

Here, the stent obtains a shape of the alveolar bone in a mouth through a CT scanning, and obtains shapes of the tooth and the gum through a plaster model formed by modeling a profile in the mouth. Then, the shapes are matched, and the implant procedure is planned through a simulation, and then the stent which may guide the procedure according to the plan is manufactured.

At this time, a guide hole which guides an insertion position of the fixture corresponding to the procedure plan while fixed in the mouth is formed at the stent. An inner circumference of the guide hole may rotatably support and guide an outer circumference of a drill used in forming the bore, and thus the bore may be formed to the precise depth and in the precise direction during the drilling operation.

Also, the fixture is inserted into the bore formed through the drilling operation, and a hex hole is formed in the fixture, and the provisional crown (the healing abutment/the cover screw) or a hex protrusion of the abutment is inserted and fixed into the hex hole.

The hex hole and the hex protrusion are formed in a polygonal shape for pressure dispersion, and the hex protrusion may be inserted into the hex hole at a certain angle. However, in the related art, since an arrangement angle of the hex hole in the fixture cannot be aligned constantly, an insertion angle of the provisional crown or the abutment is changed depending on the insertion angle of the fixture.

The cover screw of the provisional crown serves to prevent foods from permeating a space in the fixture, and the healing abutment serves to hold a shape of the restoring gum and also to perform a function of the cover screw. At this time, when the insertion angle of the fixture is different from the arrangement angle of the healing abutment according to the implant procedure plan, the fixture should be repeatedly inserted and withdrawn to correct the arrangement angle of the fixture. In this process, the alveolar bone may be damaged or lost, and thus a restoring period thereof is increased.

Also, a polygonal protrusion to which the final crown is coupled is formed at an upper side of the abutment, and a direction of the polygonal protrusion is changed depending on an insertion angle of the abutment. Therefore, when the final crown is manufactured, it is necessary to reflect the direction of the abutment after the insertion of the fixture, and thus an image in a patient's mouth should be additionally obtained in a state in which the abutment is coupled.

Then, the abutment or the final crown should be manufactured according to the obtained image, and thus a period of time for the implant procedure is increased.

SUMMARY OF THE INVENTION

The present invention is directed to a dental implant insertion set and a manufacturing method thereof.

According to an aspect of the present invention, there is provided a dental implant insertion set including a crown designed according to a three-dimensional procedure guide image obtained by matching a three-dimensional image of periodontal tissue in a patient's mouth through a CT scanning and a three-dimensional outer shape image corresponding to the three-dimensional image through an oral scanning; a fixture which has a hex hole formed therein and of which an insertion angle is set so that the hex hole is aligned corresponding to an arrangement angle of the crown; a guide stent including a stent body formed with a profile set through the three-dimensional procedure guide image to be fixed while covering the periodontal tissue, and having a coupling hole formed at an insertion position of the fixture, and a sleeve inserted into the coupling hole, having a guide hole formed at an inner circumference thereof to rotatably support an implant drill, and also having a guide protrusion formed at one side of an outer circumference to guide an insertion angle of the fixture; and an abutment having a hex protrusion formed at a lower portion thereof to be matched with and fixed into the hex hole, such that the crown is aligned and fixed.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
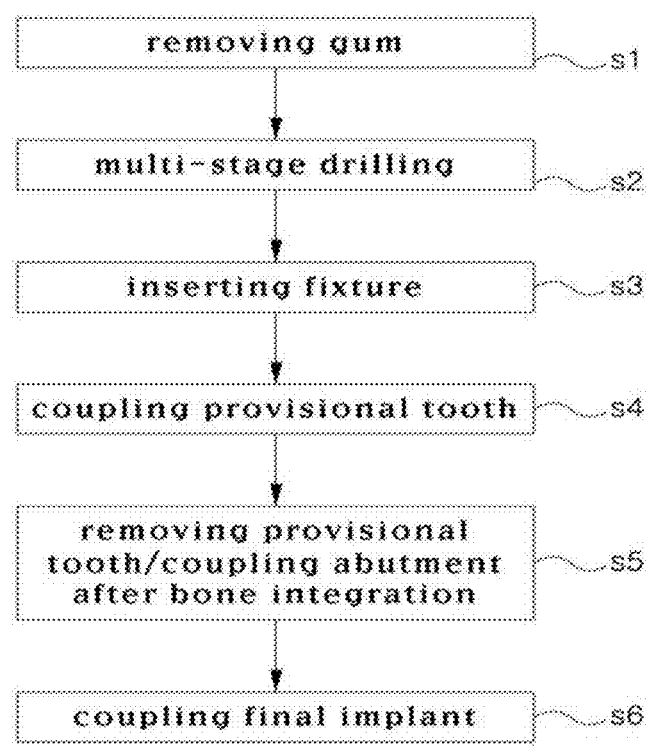
FIG. 1 is a flowchart illustrating a conventional implant procedure.

Exemplary embodiments of the present invention will be described in detail below with reference to the accompanying drawings, wherein like reference numerals refer to like or corresponding elements throughout the drawings and repeated description thereof will be omitted.

As illustrated in FIGS. 2 to 8, a dental implant insertion set according to one embodiment of the present invention includes a crown 5, a fixture 3, a guide stent 100, and an abutment 6.

Here, the crown 5 is designed according to a three-dimensional procedure guide image obtained through a three-dimensional image inside a mouth and a three-dimensional outer shape image. At this time, the crown 5 means an artificial tooth which is fixed to a tooth defect portion of a patient so as to replace a defective tooth.

At this time, the three-dimensional image may be obtained through a CT scanning or the like and includes information on periodontal tissues in the mouth, such as a dental crown (an upper side of a tooth exposed to an outside of gum), a dental root (a lower side of the tooth in the gum which is coupled with an alveolar bone), the alveolar bone and a nerve.

Also, the three-dimensional outer shape image may be obtained through an oral scanning, and includes a shape of the dental crown among the periodontal tissues in the mouth, and a shape of the gum around the dental root which is not clearly indicated on the three-dimensional image.

At this time, the three-dimensional image and the three-dimensional outer shape image may be matched based on the dental crown of the tooth which is a common portion of the two images, and thus the three-dimensional procedure guide image may be obtained. Here, the three-dimensional procedure guide image may include comprehensive information on the shapes of the dental crown and the gum, the dental root in the gum and the alveolar bone.

The crown may be designed through the three-dimensional procedure guide image. Here, the three-dimensional image and the three-dimensional outer shape image may be formed and obtained by converting the information on the periodontal tissues in the patient's mouth into three-dimensional vector data through a CT scanner or an oral scanner.

The three-dimensional vector data of each image may be digitalized and stored in a memory device of a computer, and an image processing operation in which each image is overlapped based on the computer may be performed. At this time, the information on the periodontal tissues included in the three-dimensional image and the information on the periodontal tissues included in the three-dimensional outer shape image may be combined. That is, the shape of the gum around the dental root may be combined with the shape information on the dental root and the alveolar bone in the gum, and thus the comprehensive information for the implant procedure may be provided.

The three-dimensional procedure guide image may be obtained by a computer-based simulation program using the digitalized three-dimensional image and three-dimensional outer shape image. An implant result after completion of the implant procedure, such as occlusion of teeth and a shape thereof, may be predicted through the three-dimensional procedure guide image and the crown designed through the simulation program. Therefore, the predicted result may be shared with the patient, a dental technical laboratory, or the like, and thus the arrangement angle and the shape of the crown which will be finally inserted may be precisely designed and manufactured.

At this time, the simulation program transmits information on coordinates and images of a three-dimensional shape of the crown to a manufacturing apparatus, and thus the crown may be manufactured. The manufacturing apparatus may be a milling machine, a 3D printer or the like, which produces a complete product corresponding to the input three-dimensional coordinates or three-dimensional image information.

Meanwhile, the fixture 3 which replaces the dental root of the tooth is inserted into an alveolar bone 2, and the abutment 6 and the crown 5 are fixed to an upper portion thereof. The fixture 3 may be formed to have various diameters according to a kind of original tooth to be replaced. The fixture 3 has a screw thread which is formed along an outer circumference thereof so as to be inserted and fixed into the alveolar bone, and a hex hole 3a which is formed therein to have a hexagonal or polygonal shape and in which the abutment 6 is inserted and fixed is formed therein.

Since a lower portion of the abutment 6 is matched with the hex hole 3a, the abutment may be completely inserted into the hex hole 3a in only a predetermined direction. At this time, a rotating angle of the fixture 3 in an insertion process is set so that the hex hole 3a formed in the fixture 3 is aligned corresponding to the arrangement angle of the crown 5 in consideration of a relationship between the crown 5 and adjacent teeth.

That is, an insertion angle of the fixture 3 is set so that a direction of the hex hole 3a is aligned corresponding to the arrangement angle of the crown 5. The abutment 6 is inserted and fixed into the fixture 3, which is inserted into the alveolar bone 2 at the preset insertion angle, depending on the direction of the aligned hex hole 3a. Also, the crown 5 may be coupled to the abutment 6, which is aligned by the hex hole 3a, so as to correspond to the designed arrangement angle.

Meanwhile, the guide stent 100 includes a stent body 10 and a sleeve 20. Here, the guide stent 100 is formed to have a profile corresponding to the three-dimensional procedure guide image obtained through the three-dimensional outer shape image and the three-dimensional image inside the mouth, and serves to guide the implant procedure to be performed.

Specifically, the three-dimensional procedure guide image includes the three-dimensional image obtained with respect to the alveolar bone 2 and the tooth in the mouth through the CT scanning, and the three-dimensional outer shape image obtained with respect to the outer shapes of the periodontal tissues of the patient, such as the tooth and a gum 1 through the oral scanning. That is, the three-dimensional procedure guide image may be obtained by matching the three-dimensional image with the three-dimensional outer shape image.

The implant procedure plan may be established after a simulation in consideration of an anatomical implant relation according to the three-dimensional procedure guide image.

In the implant procedure, internal and external conditions, such as the outer shape and the arrangement angle of the crown (the artificial tooth), a space between teeth, the arrangement and the coupling between the alveolar bone and the fixture according to nervous tissue, density and distribution of the alveolar bone, should be considered together. Therefore, when both of the three-dimensional image and the three-dimensional outer shape image rather than one of them are used, the implant procedure having high accuracy and completion may be provided.

Here, the stent body 10 is formed according to the profile preset through the three-dimensional procedure guide image so as to be fixed while covering the periodontal tissues, and a coupling hole 11 is formed at an insertion position of the fixture.

Figure 2:
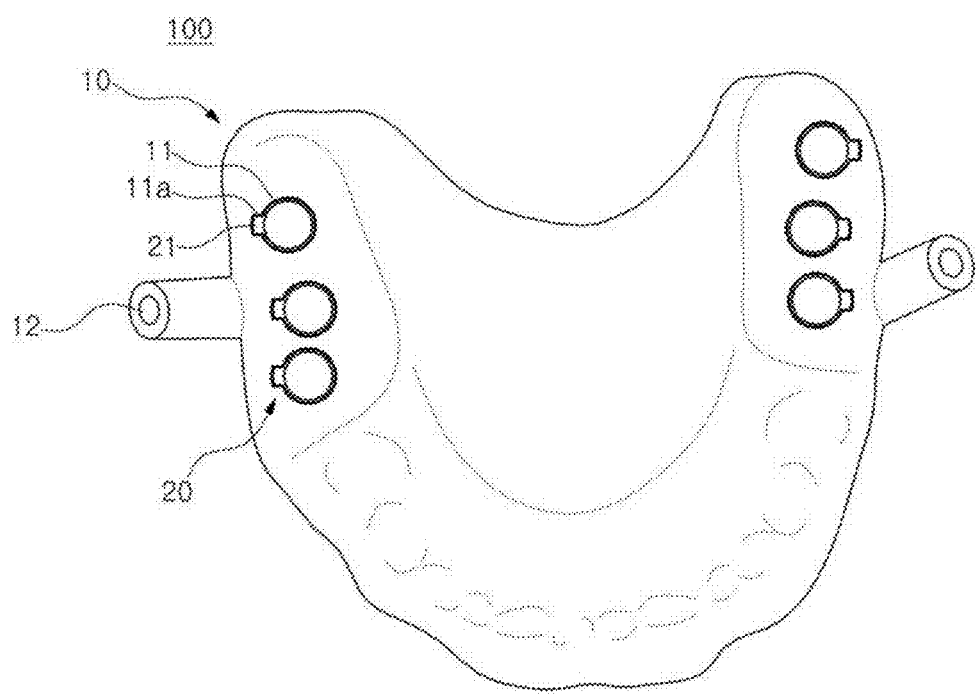
FIG. 2 is a view illustrating an example of a guide stent in a dental implant insertion set according to one embodiment of the present invention.

Specifically, referring to FIG. 2, an outer surface of the stent body 10 may be formed to have the profile preset through the three-dimensional procedure guide image, and may be inserted and fixed, while matched with the periodontal tissues.

At this time, the stent body 10 may be manufactured by the 3D printer in which a photocurable resin is cured from a bottom using UV laser, and laid in layers, and thus which forms a three-dimensional object, according to three-dimensional information of the periodontal tissues shown in the three-dimensional procedure guide image.

Also, an anchor hole 12 may be provided at a side portion of the stent body 10. An anchor pin is inserted into the anchor hole 12. The anchor pin is inserted and fixed into the patient's gum and alveolar bone, and thus the stent body 10 may be fixed in the mouth.

Therefore, the stent body 10 in a fixed state may stably guide the entire implant procedure including a drilling operation. Also, the coupling hole 11 may be provided at the stent body 10 according to an insertion position of the fixture 3 so as to correspond to the number of implants to be inserted. At this time, the sleeve 20 which guides the insertion position of the fixture according to the implant procedure plan and also guides the drilling operation forming a bore at the insertion position of the fixture is provided at the coupling hole 11 of the stent body 10.

Figure 3:
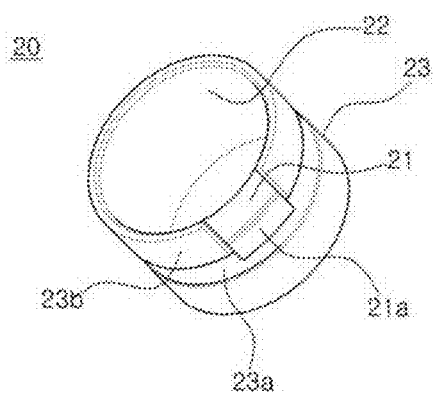
FIG. 3 is a perspective view illustrating a sleeve of the guide stent in the dental implant insertion set according to one embodiment of the present invention.

Further, referring to FIG. 3, the sleeve 20 is inserted and coupled into each coupling hole 11, and includes a hollow bushing part 23 and a guide protrusion 21. Here, the coupling hole 11 is formed to correspond to the insertion position of the fixture, and a guide hole 22 which rotatably supports an implant drill along an inner circumference thereof is formed at the hollow bushing part 23.

The drill forming the bore in which the fixture is inserted is rotatably supported by the guide hole 22, and the guide hole 22 serves to guide a depth, a direction and a diameter of the bore. Therefore, the guide hole 22 may be provided to have a predetermined diameter which is in contact with an outer circumferential surface of the drill and guides the drill. An upper rim of the guide hole 22 may be formed within a predetermined height range capable of controlling an insertion depth of the drill.

Also, the hollow bushing part 23 may be formed of a brass material, and thus may firmly support a stress due to high speed rotation of the drill, may reduce a friction force upon the rotation of the drill, thereby reducing frictional heat, and also may prevent deformation of the guide hole 22 due to the stress or the frictional heat.

Therefore, the drill may be accurately and stably guided, and an accuracy of the bore may be enhanced, and thus the implant procedure having high completion may be performed, and vibration or damage of the drill due to the deformation may be prevented.

Figure 4:
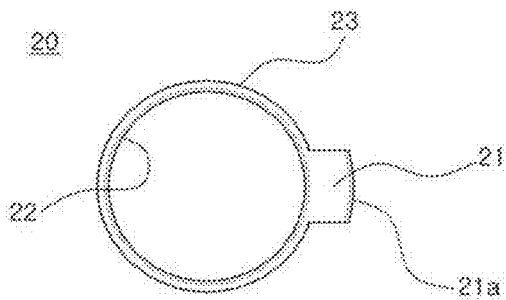
FIG. 4 is a plan view illustrating the sleeve of the guide stent in the dental implant insertion set according to one embodiment of the present invention.

Referring to FIGS. 2 to 4, the guide protrusion 21 is formed to protrude from one side of an outer circumference of the hollow bushing part 23, and fixed to one side of the coupling hole 11. Here, the guide protrusion 21 may prevent a rotational movement of the sleeve 20, when the sleeve 20 is inserted and fixed into the coupling hole 11.

That is, since an inner circumferential surface of the hollow bushing part 23 is in contact with the outer circumferential surface of the drill, a force which rotates the hollow bushing part 23 acts on the hollow bushing part 23 due to the rotation of the drill. At this time, since the guide protrusion 21 is fixed to one side of the coupling hole 11 of the guide stent 100, the hollow bushing part 23 may be prevented from being rotationally moved and thus separated. Therefore, even though the drill inserted into the hollow bushing part 23 is rotated, the guide protrusion 21 is restricted and fixed, and thus the position of the drill may be accurately maintained, and stable guide performance may be provided.

Also, a coupling surface 23b which is surface roughness processed in a circumferential direction of the hollow bushing part 23 may be formed at the outer circumferential surface of the hollow bushing part 23. Therefore, when the hollow bushing part 23 and the coupling hole 11 are combined by an adhesive or the like, a contact area is increased, and thus a binding force may be enhanced. Of course, a separation preventing groove 23a may be formed at the outer circumferential surface of the hollow bushing part 23 in the circumferential direction thereof. At this time, a separation preventing protrusion which is formed at the inner circumferential surface of the coupling hole 11 in a circumferential direction thereof may be inserted and caught in the separation preventing groove 23a.

Thus, the sleeve 20 may be fixed not to be rotated by the guide protrusion 21, and the separation preventing groove 23a and the separation preventing protrusion may be coupled with each other and thus the sleeve 20 may be fixed to the coupling hole 11. When the sleeve 20 is simply inserted into the coupling hole 11, while aligned according to a direction thereof, and then rotated, the guide protrusion 21 is automatically aligned to the preset position, and thus assemblability of a product may be enhanced.

Figure 5A:
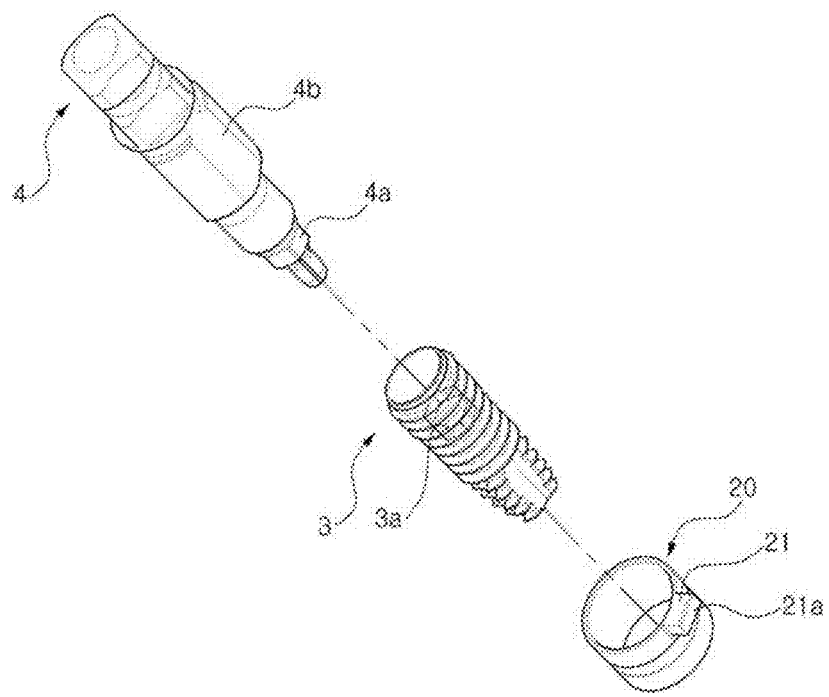
FIGS. 5A and 5B are views illustrating an example of an alignment of a fixture in the dental implant insertion set according to one embodiment of the present invention.

Meanwhile, referring to FIG. 5A, a guide hex protrusion 4a which is inserted into the hex hole 3a may be formed at a lower portion of an implant connector 4, and the fixture 3 may be aligned corresponding to the arrangement angle of the crown 5 and then inserted.

Here, when the bore is formed at the insertion position of the fixture, the implant connector 4 may be used to insert the fixture 3 into the bore, and an insertion angle of the fixture 3 may be controlled through the guide hex protrusion 4a coupled into the hex hole 3a of the fixture 3. That is, while the fixture 3 is inserted and coupled into the guide hex protrusion 4a of the implant connector 4, the fixture 3 may be inserted into the bore formed in advance.

Figure 5B:
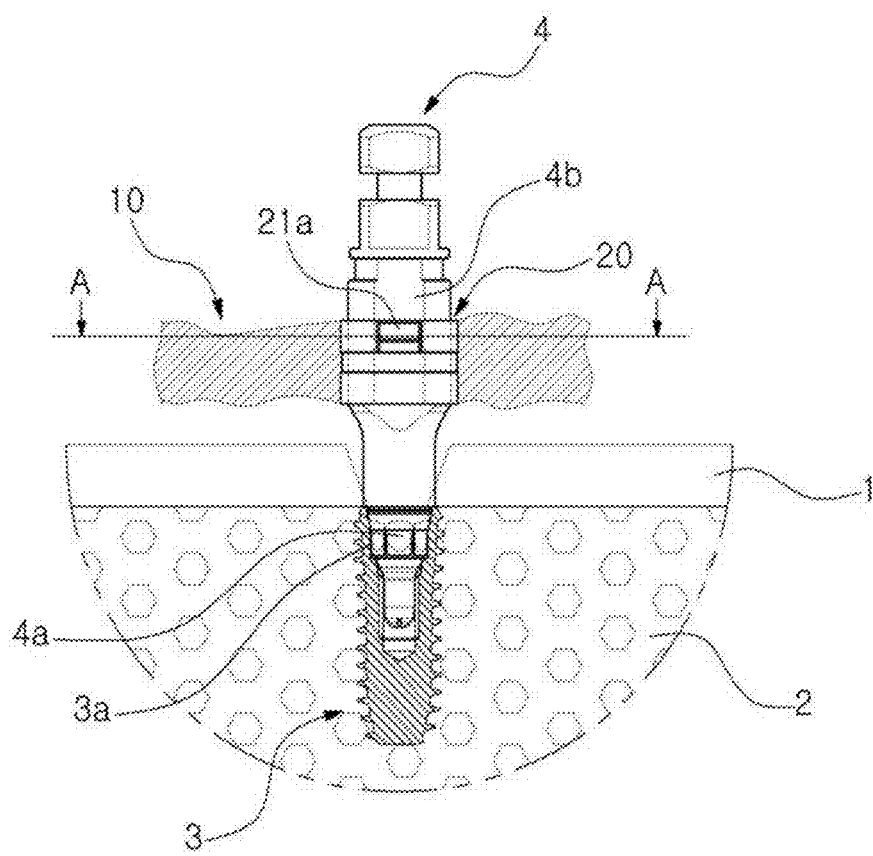
Figure 5C:
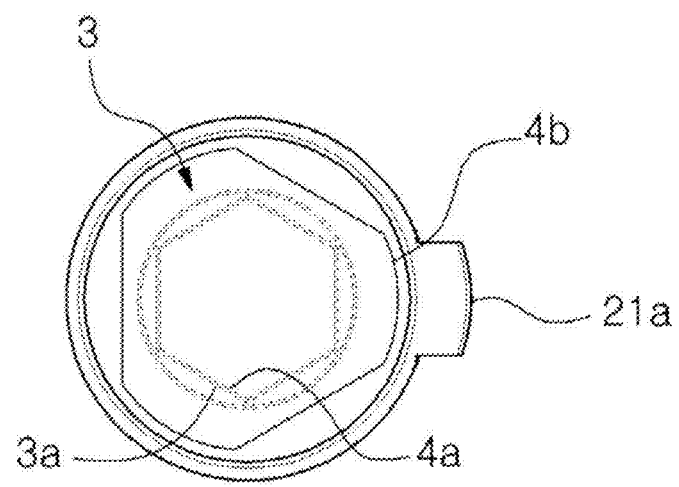
FIG. 5C is a projected cross-sectional view projecting and illustrating a hex hole of the fixture and a first hex protrusion of an implant connector in a dotted line at a cross section taken along line A-A of FIG. 5B.

Specifically, referring to FIGS. 5B and 5C, in a state in which the guide hex protrusion 4a is inserted and fixed into the hex hole 3a formed in the fixture 3 so as to be matched therewith, the fixture 3 may be inserted into the bore.

At this time, the guide hex protrusion 4a may be completely inserted into the hex hole 3a in only the preset direction. Also, an aligning surface 4b provided in parallel with one surface of the guide hex protrusion 4a may be formed at a side surface of the implant connector 4.

Here, the guide protrusion 21 may be fixed to a rim of the coupling hole 11 at a predetermined insertion guide angle, such that the abutment 6 and the fixture 3 are aligned according to the arrangement angle of the final crown 5 coupled in the mouth, when the three-dimensional procedure guide image is obtained.

At this time, when the fixture 3 passes through the guide hole, while coupled to an end of the implant connector 4, and is then rotationally inserted into the bore, the aligning surface 4b of the implant connector 4 and an outer surface 21a of the guide protrusion 21 are aligned in parallel with each other. Therefore, the fixture 3 may be inserted and fixed into the bore at the predetermined insertion angle.

That is, the guide protrusion 21 serves as a reference which aligns a direction of the hex hole 3a of the fixture 3. By aligning a direction of the implant connector 4 aligned and coupled in the direction of the hex hole 3a of the fixture 3 to the guide protrusion 21, the direction of the hex hole 3a of the fixture 3 may be aligned.

At this time, the guide hex protrusion 4a of the implant connector 4 is provided to have the same cross section as that of a hex protrusion 6b of the abutment 6. Therefore, when the fixture is aligned through the implant connector 4, the abutment 6 may also be matched with and inserted into the hex hole 3a of the fixture 3, and thus aligned thereto. Therefore, the crown 5 coupled to the abutment 6 may be coupled into the mouth according to the three-dimensional procedure guide image.

Meanwhile, the abutment 6 has the hex protrusion 6b formed at the lower portion thereof to be matched with and fixed into the hex hole 3a and thus to fix and align the crown 5 to the arrangement angle. Here, the abutment 6 fixedly connects the crown 5 and the fixture 3, and a coupling angle thereof with the fixture 3 may be controlled by the hex protrusion 6b. Accordingly, when the fixture 3 is inserted at the preset insertion angle, a direction of the abutment 6 may be set according to an angle of the fixture 3, and thus the abutment 6 may be inserted. Also, the crown 5 may be coupled with the abutment 6 in a constant direction, and thus may be coupled at an initially designed arrangement angle.

Meanwhile, the preset arrangement angle is determined so that the hex protrusion 6b of the abutment 6 matched with the hex hole 3a of the fixture 3 is aligned corresponding to the arrangement angle of the crown manufactured according to the three-dimensional image obtaining data. A fixing position of the guide protrusion 21 is determined according to the arrangement angle, and fixed to the rim of the coupling hole 11.

Figure 6:
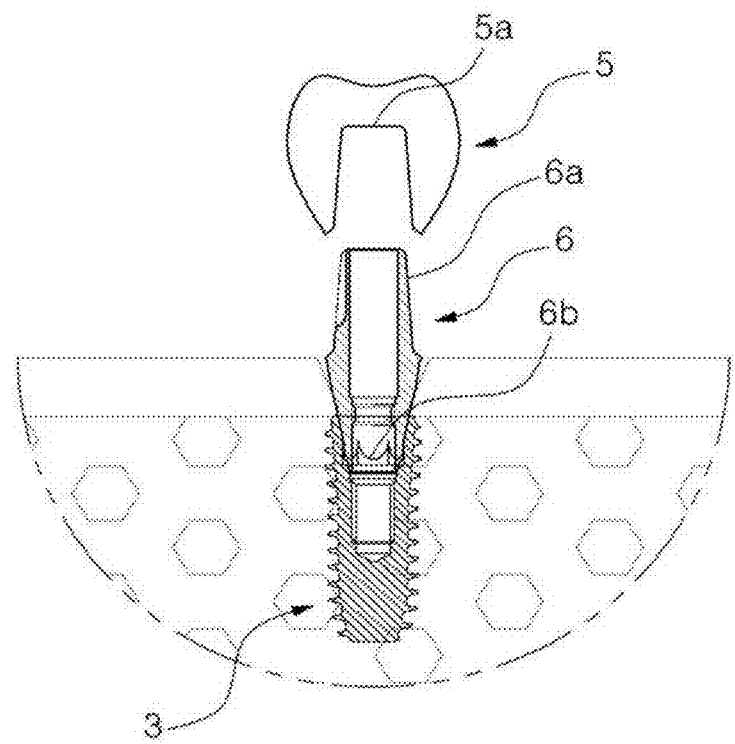
FIG. 6 is a view illustrating an example of a coupling of the fixture and an abutment in the dental implant insertion set according to one embodiment of the present invention.

Specifically, as referring to FIG. 6, the hex hole 3a may be formed in the fixture 3, and the hex protrusion 6b of the abutment 6 may be matched with and inserted into the hex hole 3a, and then may be fixed by the adhesive. At this time, the hex hole 3a and the hex protrusion 6b may be provided in a honeycomb shape not to be damaged by a pressure due to a masticatory movement of teeth. The hex protrusion 6b may be completely inserted into the hex hole 3a in only the preset direction.

Figure 7:
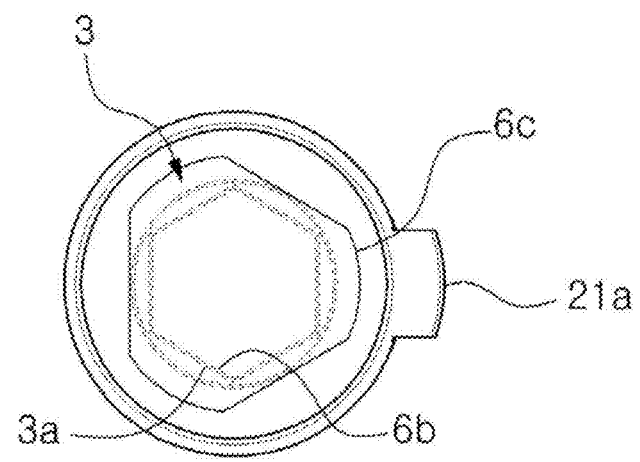
FIG. 7 is a partly projected cross-sectional view illustrating a state in which the abutment is aligned with one surface of a guide protrusion in the dental implant insertion set according to one embodiment of the present invention.

Also, referring to FIG. 7, a guide surface 6c provided in parallel with one surface of the hex protrusion 6b may be formed at the abutment 6.

Here, when the three-dimensional image obtaining data is obtained, the guide protrusion 21 may be fixed to the rim of the coupling hole 11 at the preset arrangement angle so that the abutment 6 to which the crown 5 is coupled and the fixture 3 to which the abutment 6 is coupled are aligned according to the arrangement angle of the final crown 5 coupled in the mouth. That is, the guide protrusion 21 serves as a reference which aligns the direction of the hex hole 3a of the fixture 3. Therefore, the abutment 6 which is coupled to the fixture 3 may be aligned according to a direction of the guide protrusion 21, and the crown 5 may be coupled in the mouth according to the three-dimensional image obtaining data.

Therefore, at the time when the three-dimensional image obtaining data is obtained through the CT scanning and the oral scanning, the crown and the abutment may be manufactured along with the guide stent 100, and thus a time required in the implant procedure may be remarkably reduced.

In other words, if the arrangement angle of the fixture 3 inserted into the bore is determined, the crown is not manufactured corresponding to the arrangement angle of the fixture 3, but instead, the arrangement angle of the crown may be set at a stage of manufacturing the guide stent 100. Therefore, a time for preparing the implant procedure and manufacturing various implants may be considerably reduced. Therefore, a generic technical apparatus capable of completing the removing of the gum, the drilling of the bore for the fixture insertion, the inserting of the fixture and the installing of the abutment/crown with one procedure may be provided.

At this time, an aligning groove 11a may be formed at the upper rim of the coupling hole 11 of the guide stent 100. Here, the aligning groove 11a is formed corresponding to the arrangement angle of the crown manufactured according to the three-dimensional image obtaining data. Therefore, if the hex protrusion 6b of the abutment 6 which is matched with the hex hole 3a of the fixture 3 is aligned with the preset arrangement angle of the guide protrusion 21 inserted into the aligning groove 11a, the general alignment with respect to the crown may be performed.

Specifically, the implant procedure plan is established according to the three-dimensional image obtaining data, and the coupling hole 11 is formed in the guide stent 100 to correspond to the insertion position of the fixture 3 according to the implant procedure plan.

The sleeve 20 which guides the direction and the diameter of the bore for the insertion of the fixture 3 is inserted and fixed into the coupling hole 11. The guide protrusion 21 of the sleeve 20 may be inserted into the aligning groove 11a formed in the coupling hole 11, and may be aligned and fixed at the preset arrangement angle. Like this, in the guide stent 100, when the three-dimensional image obtaining data is obtained, the aligning groove 11a is formed in the coupling hole 11 to correspond to the arrangement angle of the crown, and the guide protrusion 21 is inserted and fixed into the aligning groove 11a.

Therefore, the hex hole 3a of the fixture 3 is aligned corresponding to the position of the guide protrusion 21, and the abutment 6 is aligned to the hex hole 3a of the fixture 3 at the preset arrangement angle, and inserted therein. Therefore, the crown manufactured at the time when the guide stent 100 is manufactured may be accurately coupled into the mouth according to the implant procedure plan. At this time, a circumferential width of the guide protrusion 21 may be provided to correspond to that of the guide surface 6c, and the width of the guide surface 6c and the circumferential width of the guide protrusion 21 may be provided equally.

Therefore, if an operator aligns the abutment 6 so that the width of the guide surface 6c corresponds to the circumferential width of the guide protrusion 21, the hex protrusion 6b of the abutment 6 and the hex hole 3a of the fixture 3 in which the hex protrusion 6b is inserted and coupled to be matched therewith may be automatically aligned.

Therefore, the operator may easily align the fixture 3 and the abutment 6 so as to correspond to the arrangement angle of the crown manufactured in advance, and the procedure time may be reduced. Of course, when the fixture 3 is inserted, the operator may align the fixture 3 so as to correspond to the guide protrusion 21, while directly checking the direction of the hex hole 3a.

Also, when the direction of the hex hole 3a is not directly seen, the abutment 6 may be inserted into the fixture 3, and then a direction of the fixture 3 may be finely controlled so that the guide surface 6c is aligned with the guide protrusion 21, when the hex protrusion 6b is inserted into the hex hole 3a to be matched therewith.

At this time, since the guide surface 6c is formed at an outer side surface of the abutment 6 to be in parallel with one surface of the hex protrusion 6b, the guide surface 6c may be arranged to be aligned with the guide protrusion 21, and thus the hex protrusion 6b may be aligned.

In other words, when the operator aligns one of the guide surface 6c of the abutment 6, the hex protrusion 6b thereof and the hex hole 3a of the fixture 3, the rest may be automatically aligned. Also, as the abutment 6 is aligned, the crown 5 manufactured according to the three-dimensional procedure guide image may be coupled at the accurate arrangement angle. That is, the operator may easily perform an arranging operation so that the width of the guide surface 6c corresponds to the circumferential width of the guide protrusion 21, and thus the procedure time may be reduced. Furthermore, as the fixture 3 and the abutment 6 are automatically accurately aligned, the manufactured crown 5 may be coupled at the accurate arrangement angle, and thus convenience and accuracy of the implant procedure may be enhanced.

Of course, a marker corresponding to the hex hole 3a may be provided at an upper rim of the fixture 3 so that the direction of the hex hole 3a formed in the fixture 3 is checked from an outside. Therefore, the operator may easily check the direction of the fixture 3 and the direction of the abutment 6 coupled to the fixture 3.

Also, the outer surface 21a of the guide protrusion 21 may be arranged at a position which is aligned in parallel with one surface of the hex protrusion 6b and the guide surface 6c formed at the abutment 6 to correspond to the arrangement angle of the crown manufactured according to the three-dimensional procedure guide image. At this time, the outer surface 21a of the guide protrusion 21 may be provided to be flat.

That is, the operator may easily align one surface of the hex hole 3a of the fixture 3, one surface of the hex protrusion 6b of the abutment 6 matched with the hex hole 3a, or the guide surface 6c in parallel with one surface of the hex protrusion 6b so as to be in parallel with the outer surface 21a of the guide protrusion 21. Therefore, the abutment 6 may be automatically aligned and coupled corresponding to the arrangement angle of the crown.

Thus, after the abutment 6 is coupled to the fixture 3 inserted into the bore, the crown is not manufactured according to the arrangement angle of the abutment 6. Instead, the arrangement angle of the crown may be set at a stage in which the guide stent 100 is manufactured. Thus, the time for preparing the implant procedure and manufacturing various implants may be remarkably reduced. Therefore, when the abutment/crown is manufactured, the generic technical apparatus capable of completing the removing of the gum, the drilling of the bore for the fixture insertion, the inserting of the fixture and the installing of the abutment/crown with one procedure may be provided.

Also, the guide protrusion 21 may protrude from a single place of the outer circumference of the hollow bushing part 23. Therefore, the guide protrusion 21 may accurately guide the arrangement angle of the fixture and the arrangement angle of the abutment according to the preset arrangement angle of the crown.

Meanwhile, a coupling groove 5a in which a coupling protrusion 6a formed at an upper end of the abutment 6 is inserted so as to be matched therewith, when the fixture 3 and the abutment 6 are aligned, may be formed in the crown 5.

Specifically, the abutment 6 may be manufactured with the crown 5, and the hex protrusion 6b formed at the lower portion thereof may be inserted into the hex hole 3a of the fixture 3 to be aligned thereto. At this time, the coupling protrusion 6a may be formed at the upper portion of the abutment 6, and may be matched with and inserted into the coupling groove 5a of the crown 5.

Here, the coupling protrusion 6a is provided to have an asymmetric shape and thus to be inserted into the coupling groove 5a only in a preset direction. Therefore, when the insertion angle of the fixture 3 is set, the abutment 6 which is coupled with the fixture 3 in the constant direction may be aligned. Like this, in the case in which the abutment 6 is aligned, when the crown 5 is coupled with the abutment 6 in the constant direction, the crown 5 and the abutment 6 may be automatically aligned at the preset arrangement angle.

Figure 8:
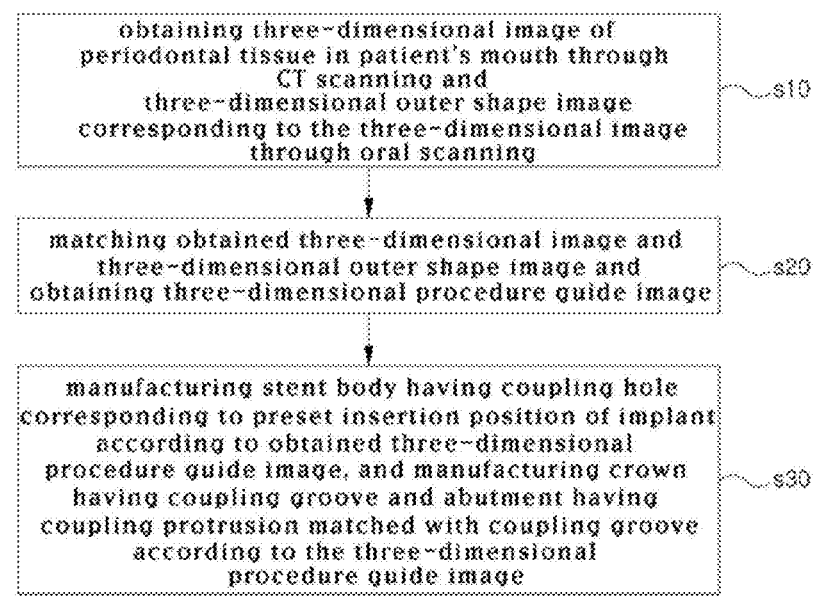
FIG. 8 is a flowchart illustrating a method of manufacturing the dental implant insertion set according to one embodiment of the present invention.

Meanwhile, a method of manufacturing the dental implant insertion set will be described with reference to FIG. 8.

First, the three-dimensional image of the periodontal tissues in the patient's mouth through the CT scanning and the three-dimensional outer shape image corresponding to the three-dimensional image through the oral scanning is obtained (s10). At this time, when the outer shape of the periodontal tissues in the patient's mouth is obtained, a separate operation of manufacturing a plaster model is not required, and the time for preparing the implant procedure is reduced, and thus the number of hospital visits for the patient may be reduced, and the patient's satisfaction in the implant procedure may be enhanced.

Also, the information on the periodontal tissues in the mouth obtained through the CT scanning may be matched with the three-dimensional outer shape image obtained by directly scanning the patient's mouth so as to obtain a more precise image matching result, and thus the accurate guide stent may be manufactured. Like this, since the accurate guide stent in which accurate diagnosis and more precise implant design are reflected is manufactured, the accurate implant procedure may be performed without correction of the procedure plan through an obtaining of an additional image at a stage of inserting the abutment or coupling the crown after the insertion of the fixture.

Therefore, by manufacturing the abutment and the crown with the manufacturing of the guide stent, the generic technical apparatus capable of completing the inserting of the fixture and the installing of the abutment/crown with one procedure after the manufacturing of the guide stent may be provided.

Meanwhile, when the three-dimensional image and the three-dimensional outer shape image are obtained (s10), the three-dimensional procedure guide image is obtained by matching the three-dimensional image with the three-dimensional outer shape image (s20). Here, an image matching method to obtain the three-dimensional procedure guide image may be variously performed, and this will be described in detail in another embodiment of the present invention which will be described later. Of course, the above-described image matching method is just an example, and a method of matching different kinds of images using an image matching reference point may be performed variously.

Subsequently, the stent body in which a through-hole is formed corresponding to the implant insertion position preset according to the three-dimensional procedure guide image is manufactured. The crown in which the coupling groove is formed according to the three-dimensional procedure guide image and the abutment in which the coupling protrusion matched with the coupling groove is formed are manufactured (s30).

In a stage of diagnosing the dental implant and manufacturing the guide stent, the final implant may be designed and manufactured together through the accurate procedure plan using the three-dimensional procedure guide image and the guide stent guiding the procedure plan. Therefore, the time for preparing the implant procedure and manufacturing the implant may be remarkably reduced. Thus, the generic technical apparatus capable of completing the removing of the gum, the drilling of the bore for the fixture insertion, the inserting of the fixture and the installing of the abutment/crown with one procedure may be provided.

Meanwhile, the implant procedure using the dental implant insertion set will be described. First, the operator diagnoses a defective tooth in the patient's mouth, and obtains the three-dimensional outer shape image and the three-dimensional image through the oral scanning and the CT scanning. The three-dimensional procedure guide image is obtained by matching the obtained images, and the detailed procedure plan is established through a simulation system. For example, the direction, the depth and the diameter of the bore are set according to distribution of the alveolar bone or a kind of the defective tooth, and the fixture which will be inserted into the bore is selected.

The guide stent which guides formation of the bore is designed according to the established procedure plan. At this time, the guide stent includes the guide protrusion which guides the insertion angle of the fixture, and the abutment which will be coupled to the fixture and the crown which will be coupled to the abutment are designed according to the insertion angle of the fixture. When the guide stent, the crown and the abutment are manufactured, the implant procedure may be performed using the guide stent.

First, the guide stent is fixed in the patient's mouth, and then the bore is formed according to the guiding of the guide hole. At this time, the fixture may be inserted into the formed bore, and in the insertion process, the fixture may be inserted into the bore through the implant connector, while aligned with the guide protrusion.

If the fixture is inserted, the manufactured abutment is inserted and fixed thereto. After the abutment is fixed, the crown is coupled, and thus the implant procedure is completed. At this time, the coupling protrusion of the abutment and the coupling groove of the crown are provided to be coupled with each other in only the constant direction. Therefore, when the abutment is aligned in the constant direction according to the insertion angle of the fixture, the abutment and the crown are automatically aligned in the constant direction, and thus the crown may be coupled at the preset arrangement angle.

Of course, the coupling protrusion of the abutment and the coupling groove of the crown may be provided in the form of a polygonal shape so as to be matched and coupled with each other in only the preset direction. While the crown and the abutment corresponding to the insertion angle of the fixture are manufactured, it is not necessary to insert a healing abutment which is manufactured to have a predetermined dimension and to prevent the hex hole of the fixture from being blocked by restored gum. Therefore, since the previously manufactured abutment may be inserted according to an initially designed tooth restoring plan, the procedure operation is very simple, and also since the number of hospital visits for the patient is reduced, the convenience of the implant procedure may be enhanced.

That is, at the time when the three-dimensional procedure guide image is obtained through the CT scanning and the oral scanning, the guide stent is manufactured, and the crown and the abutment are also manufactured at the same time, and thus the time for the implant procedure may be reduced.

Of course, before the final crown is coupled after the abutment is fixed, an provisional crown capable of being coupled to the abutment with a tolerance of 3 degrees or less may be coupled. After the provisional crown and the abutment are coupled, a waiting period of about 3 days goes by, the progress after the procedure is checked through a separate scanning, and thus the final crown may be coupled.

Therefore, through a comparative analysis between a result predicted by coupling the provisional crown having a similar shape to the final crown and an actual procedure result, the implant procedure having more accurate and high completion may be performed.

Figure 9:
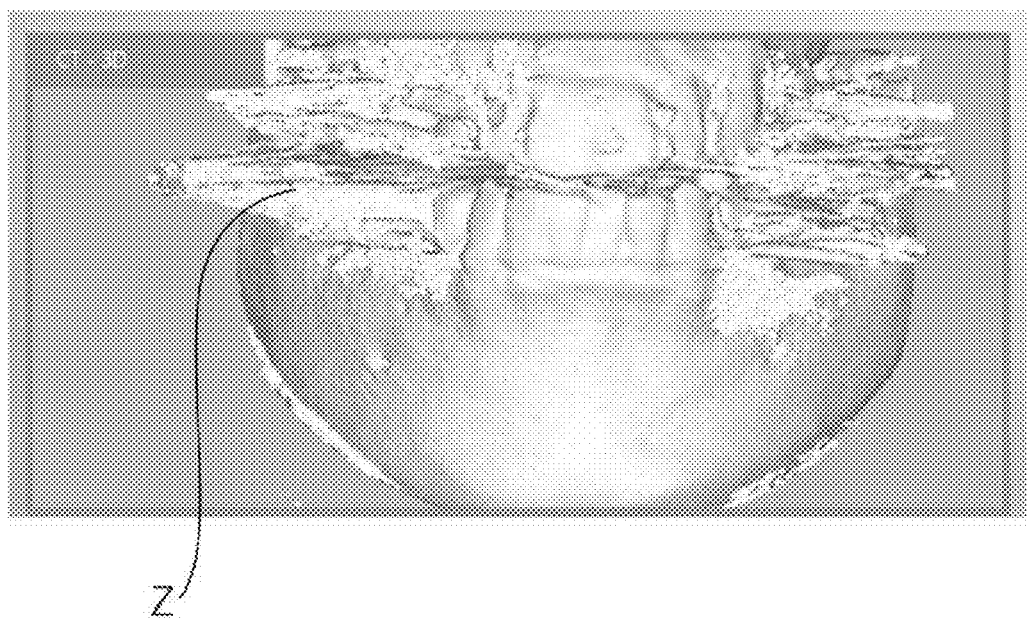
FIG. 9 is a view illustrating an example of a three-dimensional image in which a scattering is generated by a metal implant.
Figure 10:
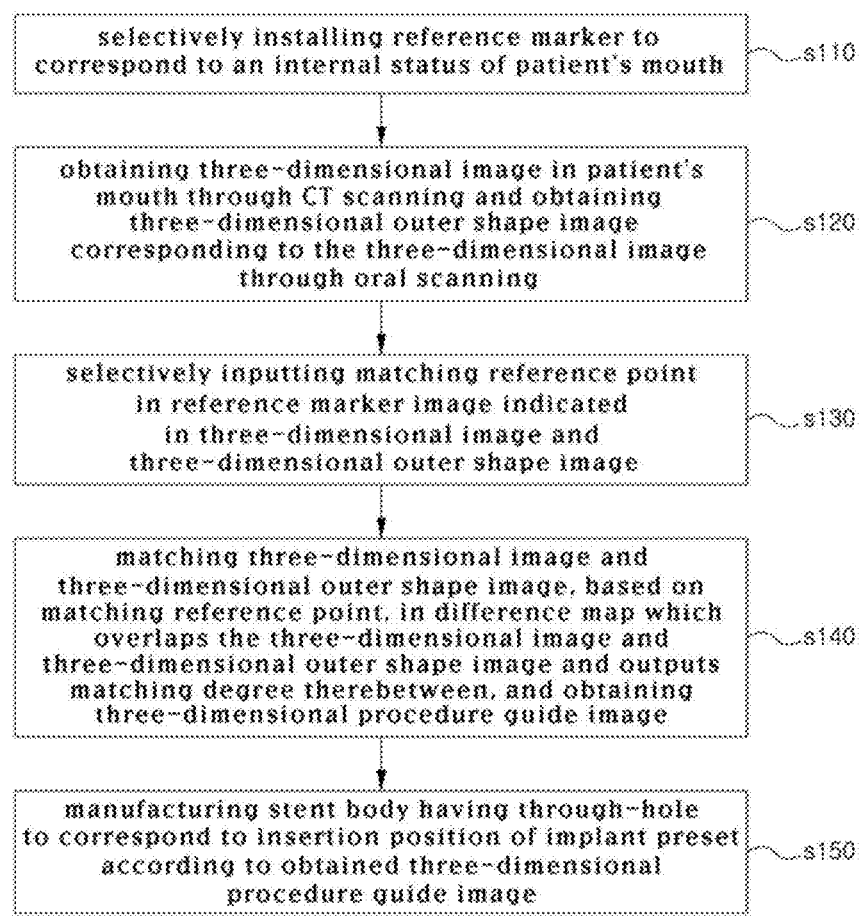
FIG. 10 is a flowchart illustrating a method of manufacturing the guide stent for implant insertion using a reference marker for attachment in a mouth according to another embodiment of the present invention.
Figure 11:
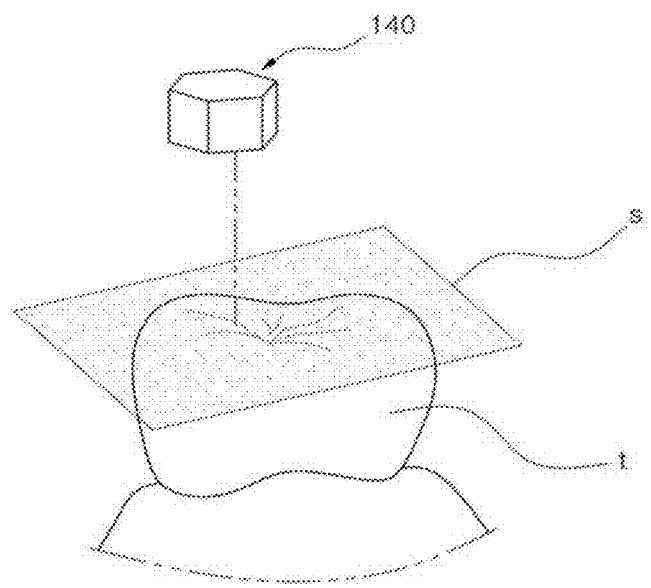
FIG. 11 is a view illustrating an example of the reference marker and an installation position thereof in the method of manufacturing the guide stent for implant insertion using the reference marker for attachment in the mouth according to another embodiment of the present invention.

Meanwhile, as illustrated in FIG. 9, when there is a metal implant in the patient's mouth, image defect z is generated by scattering of light due to the metal implant. Therefore, it is difficult to obtain an accurate three-dimensional image of the dental crown in the mouth, and thus there is a problem in that accuracy in the image matching is reduced.

Further, the problem in the image matching equally occurs even at an edentulous patient who wholly or partly has no teeth in the mouth.

As illustrated in FIGS. 10 to 15B, to solve the problem, a method of manufacturing the guide stent for the insertion of the implant using a reference marker for attachment in a mouth according to another embodiment of the present invention will be described.

First, a reference marker 140 is installed in the patient's mouth (s110). At this time, the reference marker 140 may be selectively installed according to a status in the mouth. For example, in the case in which the metal implant is inserted into the patient's mouth or in the case of the edentulous patient who has no teeth, it is preferable that the reference marker 140 be installed. Here, the term "in the mouth" includes the teeth (natural teeth and artificial teeth), the gum, the alveolar bone, the roof of the mouth and so on.

At this time, the reference marker 140 may be installed at a portion of one of upper jaw tissue and lower jaw tissue of the patient, in which one tissue faces the other tissue. For example, referring to FIG. 11, when the reference marker 140 is installed at a tooth t of the lower jaw tissue, the reference marker 140 may be installed along an occlusal surface s facing a tooth of the upper jaw tissue.

A three-dimensional image 110 in the mouth through the CT scanning and a three-dimensional outer shape image 120 corresponding to the three-dimensional image 110 through the oral scanning are obtained (s120). Then, as described above, the three-dimensional image 110 and the three-dimensional outer shape image 120 are image-matched with each other, and thus a three-dimensional procedure guide image 130 totally including the dental crown, the dental root, the shape and the density of the alveolar bone, and the shape of the gum may be generated. The guide stent 100 (of FIG. 2) may be accurately manufactured based on the three-dimensional procedure guide image 130.

Here, in the case of a general patient, a common portion between the images 110 and 120 may be crowns 112 and 122. However, in the case of the edentulous patient or the patient who has the metal implant, the reference marker 140 may be reference marker images 115 and 125 indicated in the images 110 and 120, respectively.

For example, referring to FIG. 9, when there is the metal implant in the patient mouth, the defect z may occur in the dental crown image due to the scattering of light. Due to the image defect z, the common portion between the three-dimensional image 110 and the three-dimensional outer shape image 120 is reduced, and it is difficult to precisely perform the image matching.

At this time, as the reference marker 140 is installed at the occlusal surface s of the metal implant or the tooth t, a reference marker image 115 which is not distorted by the scattering of light may be indicated at an upper portion of the defect z. The reference marker image 115 may be accurately indicated on the three-dimensional image 110 obtained by three-dimensionally arranging each tomography image in the mouth without distortion due to the light scattering of the metal implant.

Like this, in the case in which the distortion occurs on the three-dimensional image 110 due to the metal implant, or in the case which has no teeth and in which the common portion between the images 110 and 120 for the image matching is insufficient, the reference marker 140 may serves as a specific reference point for the image matching. Through the reference marker 140, more accurate image matching results corresponding to various states in the patient's mouth may be obtained, and thus the accurate guide stent which accurately guides the implant procedure plan may be manufactured.

Therefore, the implant procedure may be accurately performed in a stage of inserting the abutment or coupling the crown after the insertion of the fixture. Also, the custom abutment and crown are manufactured together with the guide stent, and thus the generic technical apparatus capable of completing the inserting of the fixture and the installing of the abutment/crown with one procedure after the manufacturing of the guide stent may be provided.

Figure 12:
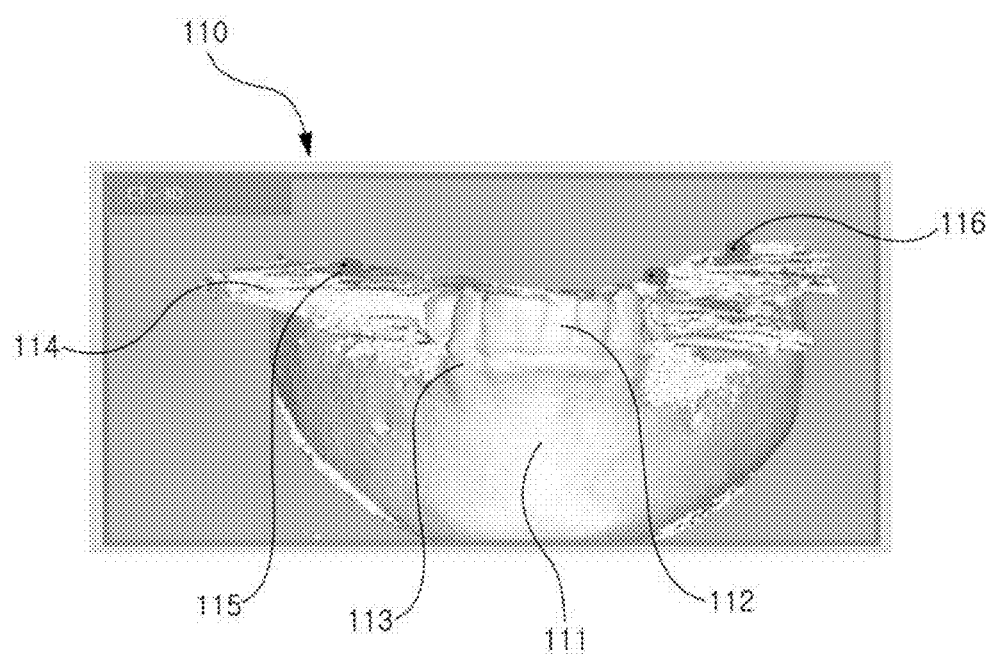
FIG. 12 is a view illustrating an example of a three-dimensional image of the method of manufacturing the guide stent for implant insertion using the reference marker for attachment in the mouth according to another embodiment of the present invention.
Figure 13:
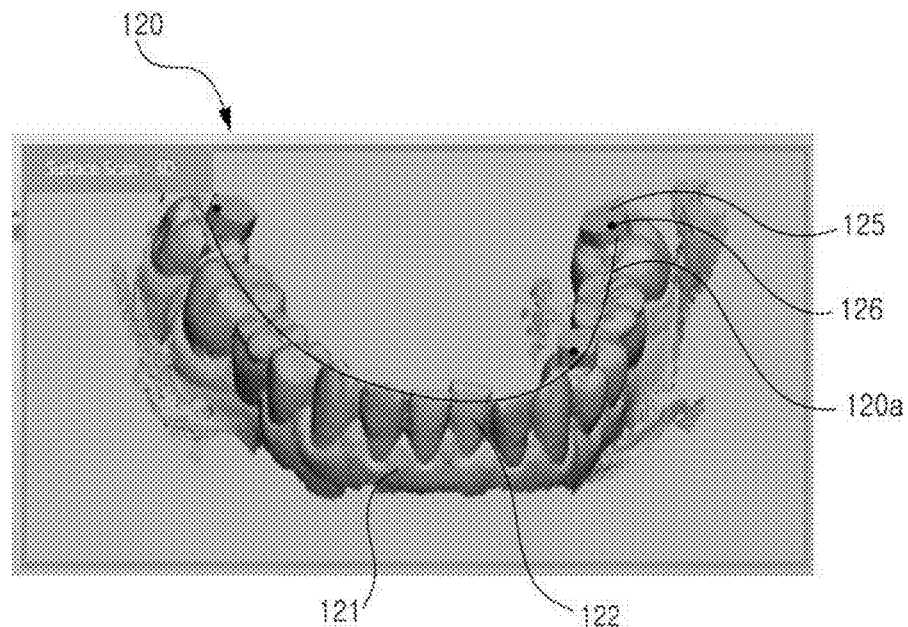
FIG. 13 is a view illustrating an example of a three-dimensional outer shape image of the method of manufacturing the guide stent for implant insertion using the reference marker for attachment in the mouth according to another embodiment of the present invention.

Meanwhile, referring to FIGS. 12 and 13, when the three-dimensional image 110 and the three-dimensional outer shape image 120 are obtained (s120), matching reference points 116 and 126 in the reference marker images 115 and 125 indicated in the three-dimensional image 110 and the three-dimensional outer shape image 120 are selectively received.

Here, the reference marker 140 may be formed of a radio-opacity material, and may be formed of alumina or the like. At this time, a density of the reference marker 140 may be 2 to 8 g/cm$^3$.

Specifically, in the case in which the density of the reference marker 140 is less than 2 g/cm$^2$, when the three-dimensional image 110 is obtained through the CT scanning, the reference marker 140 is similar to an image value of soft tissue in the mouth, such as the gum, and thus the reference marker image 115 may be disappeared. In the case in which the density of the reference marker 140 is more than 8 g/cm$^2$, the reference marker 140 causes the scattering of light, like the metal implant, and thus the distortion or the defect may occur in the image. To enhance the accuracy, it is more preferable that the density of the reference marker 140 may be 3 to 4 g/cm$^2$.

Since the reference marker 140 is formed of the radio-opacity material, the reference marker 140 may be indicated similarly to the teeth 112 and 113 or an alveolar bone 111 on the three-dimensional image 110. Since the three-dimensional outer shape image 120 is obtained by collecting outer shape information through the oral scanning, an outer shape of the reference marker 140 may be indicated on the three-dimensional outer shape image 120, as it is.

At this time, the operator may select and input the matching reference points 116 and 126 on the reference marker images 115 and 125 indicated in each image 110, 120. Here, the reference marker may be installed at one or more places in the patient's mouth. The operator may input the matching reference point on a similar position of each pair of reference marker images 115 and 125 indicated in the three-dimensional image 110 and three-dimensional outer shape image 120.

For example, when three reference markers are installed in the patient's mouth, the matching reference point is input on a mutually corresponding position of each of the plurality of reference marker images indicated in the three-dimensional image 110 and three-dimensional outer shape image 120.

Therefore, when the three-dimensional image 110 and three-dimensional outer shape image 120 are overlapped with each other, an initial difference map 130 having a small error may be obtained, and a correcting operation of each image 110, 120 may be smoothly performed in a next image matching process.

Also, the reference marker may be formed in a shape having a certain volume, such as a cylinder and a polyprism. One of opposite upper and lower surfaces of the reference marker is attached to an inner side of the patient's mouth, and the other surface which is spaced in parallel from the one surface may be used as the matching reference. At this time, the matching reference points 116 and 126 may be input on an edge of the other surface used as the matching reference.

Figure 14:
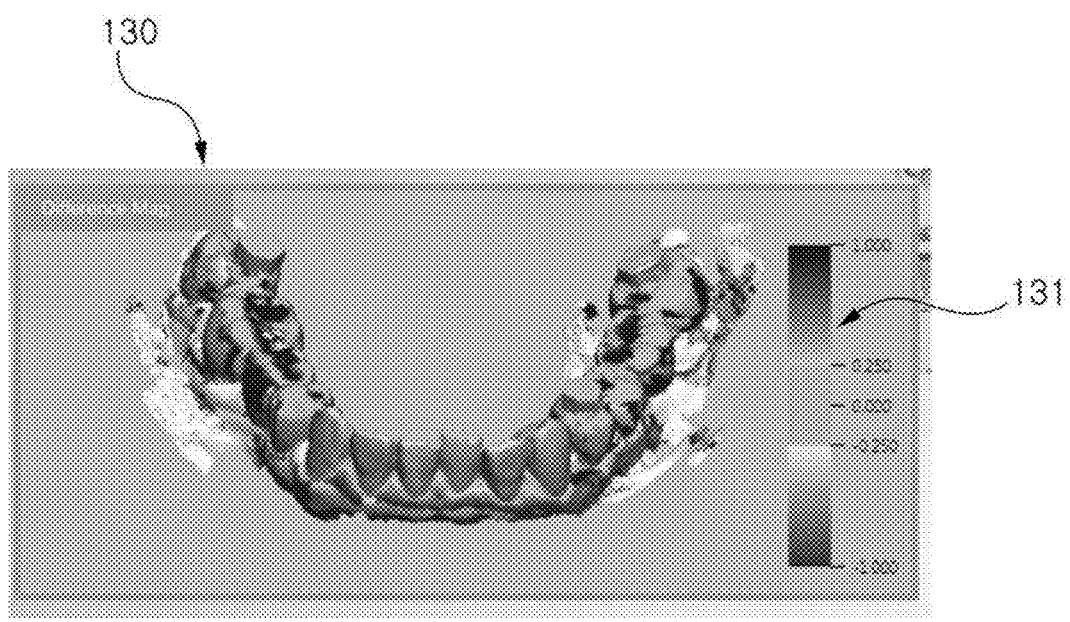
FIG. 14 is a view illustrating an example of a difference map of the method of manufacturing the guide stent for implant insertion using the reference marker for attachment in the mouth according to another embodiment of the present invention.

Meanwhile, referring to FIG. 14, the matching reference points 116 and 126 are selected and input in the reference marker images 115 and 125 (s130). Then, the three-dimensional image 110 and the three-dimensional outer shape image 120 are matched, based on the matching reference points 116 and 126, in the difference map 130 in which the three-dimensional image 110 and the three-dimensional outer shape image 120 are overlapped and a matching degree between the images 110 and 120 in each pixel is output, and thus the three-dimensional procedure guide image is obtained (s140).

Here, as the information in the patient's mouth is converted into the three-dimensional vector data by a CT scanner or an oral scanner, the three-dimensional image 110 and the three-dimensional outer shape image 120 may be formed and obtained.

The three-dimensional vector data of each image may be digitalized and stored in a memory device of a computer, and a computer-based image processing operation in which each image is overlapped may be performed. At this time, the three-dimensional image 110 and the three-dimensional outer shape image 120 are overlapped based on the matching reference points mutually corresponding in the initial image processing operation, and thus the difference map 130 may be formed.

Here, the difference map 130 includes the information on the inner side of the mouth included in the three-dimensional image 110 in one set, and also includes the information on the outer shape of the inner side of the mouth included in the three-dimensional outer shape image 120 in one set. And the overlapped image in which each set of information is connected based on the matching reference points 116 and 126 may be displayed. Through the overlapped image, the information on the dental crown 112, the dental root 113, and the shape and density of the alveolar bone 111 of the three-dimensional image 110 and the information on the dental crown 122 and the gum 121 of the three-dimensional outer shape image 120 may be combined, and thus the comprehensive information may be provided.

At this time, the three-dimensional image 110 and the three-dimensional outer shape image 120 may be combined based on a common portion which is commonly indicated on the two images 110 and 120. That is, the information on the dental root 113, the alveolar bone 111 and the gum 121 may be mutually matched through a relationship among the common portion, the dental root 113 and the alveolar bone 111 in the three-dimensional image 110 and a relationship between the common portion and the gum 121 in the three-dimensional outer shape image 120, and then may be displayed as combined information.

Here, in the case in which the metal implant is inserted, or in the case of the edentulous patient who has no dental crown, the common portions which are commonly indicated on the two images 110 and 120 may serve as the reference marker images 115 and 125.

Also, the matching degree which is a degree of similarity between the three-dimensional image 110 and the three-dimensional outer shape image 120 is indicated by a matching error between the two images 110 and 120. At this time, if an absolute value of the matching error becomes small, it means that the two images are accurately matched and overlapped, and thus it may be expressed that the matching degree is high.

And if the absolute value of the matching error becomes great, it means that the two images are erroneously matched and overlapped, and thus it may be expressed that the matching degree is low. That is, when the matching error is 0, the matching degree is the highest, and it may be expressed that the matching degree is reduced in proportion to the absolute value of the matching error. For example, when the three-dimensional image 110 and the three-dimensional outer shape image 120 are overlapped, the matching degree may indicate a protruding or recessed degree of a surface of one image from a surface of the other image.

At this time, the matching degree may be calculated by the three-dimensional vector data of each image. That is, the three-dimensional vector data of each image may be converted into the same coordinate system, and height information of the surface of each image may be indicated as a numerical value through the three-dimensional vector data converted into the same coordinate system.

The protruding or recessed degree of the surface of one image from the surface of the other image may be calculated by comparing the height of the surface of each image, while the images are overlapped. That is, when the protruding or recessed degree is high, the absolute value of the matching error is great, and this means that the matching degree is low. At this time, when the surface of the other image protrudes more than the surface of the one image, the matching error has a positive value, and when the surface of the other image is recessed more than the surface of the one image, the matching error has a negative value.

And the difference map 130 is formed by overlapping each image 110, 120, and the matching degree is indicated in each pixel. That is, the difference map 130 includes each of the information on the three-dimensional image 110 and the information on the three-dimensional outer shape image 120 as each of set information, and indicates the matching degree between the images overlapped in each pixel.

At this time, the image matching is performed to increase the matching degree indicated in each pixel of the difference map 130. When the image matching is completed, a layer in which the matching degree is indicated is removed, and thus the three-dimensional procedure guide image including both of the three-dimensional image 110 and the three-dimensional outer shape image 120 may be obtained.

Through the obtained three-dimensional procedure guide image, the guide stent which guides the implant procedure may be manufactured, and the implants necessary for the implant procedure, such as the custom abutment and the crown, may be manufactured.

At this time, the three-dimensional procedure guide image may be obtained using the digitalized vector information of the three-dimensional image 110 and the three-dimensional outer shape image 120. Specifically, the image processing operations, such as a rotation and an extension/contraction of each image, and a partial angle correction, may be performed using the computer-based simulation program, and thus the matching degree with respect to the common portion of each image in the difference map 130 may be increased.

Also, the implant result predicted in connection with the obtaining of the three-dimensional procedure guide image, such as occlusion of teeth and a shape thereof, through the simulation program may be shared with the patient, the dental technical laboratory, or the like, and thus the implant procedure having higher completion may be provided.

Like this, since the more accurate procedure plan may be established through the three-dimensional procedure guide image, a separate re-measurement operation is not required in each state of the implant procedure, such as the forming of the bore, the inserting of the fixture, the manufacturing and inserting of the custom abutment and the manufacturing and inserting of the crown.

Therefore, the various implants required for a follow-up procedure may be substantially simultaneously manufactured with the guide stent, and thus the number of hospital visits for the patient and the period of time for the implant procedure may be considerably reduced. Therefore, the generic technical apparatus for one-day implant procedure, which is capable of completing the inserting of the fixture and the installing of the abutment/crown with one procedure, may be provided.

The implant result predicted by the simulation program may be formed as data which is compatible with a CAD/CAM manufacturing apparatus or the like. In the case of a simple implant, it may be immediately manufactured with calculation of the implant result by the manufacturing apparatus.

Meanwhile, when the three-dimensional procedure guide image is obtained (s140), the stent body 10 (of FIG. 2) in which the coupling hole 11 (of FIG. 2) is formed corresponding to the preset insertion position of the implant is manufactured according to the obtained three-dimensional procedure guide image (s150).

Here, in the three-dimensional procedure guide image, a tooth arrangement, a defect position, a shape and density of the alveolar bone to which the tooth is coupled, and a shape of the gum covering the alveolar bone and the dental root may be indicated in detail. Therefore, the operator may obtain detailed information including a visible outer shape of the defect position necessary for the implant procedure and the internal tissue corresponding thereto.

That is, through the three-dimensional procedure guide image, the operator may determine the insertion position of the fixture, and also may determine the direction and the depth of the bore according to the shape and the density of the alveolar bone. That is, an implant diagnosis and procedure plan necessary for the implant procedure, such as the insertion position and the insertion depth of the implant, and whether to perform a bone implant, may be established in advance.

Of course, the above-described simulation system may be used in the implant diagnosis and procedure plan. At this time, the simulation system may calculate generic information related to the implant procedure, such as a coupling force of the fixture upon insertion thereof, which can be obtained according to the direction and the depth of the bore and whether the fixture or the alveolar bone may endure a pressure required in the masticatory movement of teeth, and provide the information to the operator. An internal profile of the stent body 10 may be formed according to an outer shape profile in the patient's mouth indicated in the three-dimensional procedure guide image. As the mutual profiles are combined, the stent body 10 may be matched and coupled in the patient's mouth.

While the stent body 10 is coupled in the patient's mouth, the through-hole 11 may be disposed at a position in which the bore is formed, and a direction of the through-hole 11 may be set so as to guide the direction of the bore. Also, in the stent body 10, a thickness and a shape around the through-hole 11 may be set so as to guide the depth of the bore.

Here, the stent body 10 may be designed based on the three-dimensional procedure guide image. For example, the simulation system may calculate a profile of an internal surface of the stent body 10 in which the outer shape in the patient's mouth may be inserted, when the three-dimensional procedure guide image is input.

The position and the direction of the through-hole 11 may be calculated by an operator's input or an internal algorithm. Here, a thickness of the stent body 10 may be provided to protect the teeth during the implant procedure, and the thickness around the through-hole 11 may be provided to support the drill and thus to guide a depth of the drill.

When a design of the stent body 10 is determined according to the calculated results, information on coordinates or an image of a three-dimensional outer shape of the design may be input to the manufacturing apparatus, and thus the stent body 10 may be manufactured. Here, the manufacturing apparatus may include a precision CNC machine, a 3D printer and so on, which may produce a complete product corresponding to the three-dimensional coordinate or three-dimensional image information.

Meanwhile, the reference marker may be adhered by a resin for provisional attachment of the implant, and also may be installed at three or more points which are spaced from each other. Here, the resin for provisional attachment of the implant does not generate a toxic substance or a bad smell, does not remain residues, and may be easily removed. The reference marker may be provided to have a preset volume or larger, such that an upper surface side outline is distinguished from a side surface and visibly indicated in a cylinder or polyprism-shaped outer shape, when the CT scanning is performed.

Also, in a correcting operation in which each pair of reference marker images coincides with each other, the reference marker may be provided to have a predetermined volume or less, thereby preventing an overload of the simulation and reducing feeling of irritation, when installed in the patient's mouth. At this time, since the reference marker is installed at the three or more points which are spaced from each other a constant distance or more in the mouth, a complicated matching method, in which an outline of a single marker is extracted and then the outline of each image coincides, is not used.

That is, through a method in which the other image of each pair of reference markers is processed in a point-to-point matching manner, a process loading may be reduced, and the image matching may be performed rapidly. Through a matching in which each pair of images coincides with respect to the three reference marker, the image matching operation may be performed more accurately. Of course, the reference markers may be installed to be spaced a preset distance or more, such that the reference marker images are not overlapped during the CT scanning.

Meanwhile, each point at which the reference marker 140 is installed may be set along a position in which at least one side of the tooth, the gum and the roof of the mouth of the patient's upper and lower jaw tissues faces the other one. At this time, the tooth may include both of the natural tooth and the artificial tooth.

For example, when the reference marker 140 is installed at the patient's upper jaw tissue, each point may be set to a position in which one side of the tooth, the gum and the roof of the mouth of the patient's upper jaw tissue faces the lower jaw tissue. At this time, the facing position may be a lower surface of the tooth, the gum and the roof of the mouth.

When the reference marker 140 is installed at the patient's lower jaw tissue, each point may be set to an upper surface of the tooth t and the gum of the lower jaw tissue. Therefore, in the case in which there is the metal implant in the patient's mouth, even though there is a portion in which the scattering of light due to the metal implant occurs on the three-dimensional image 110, the reference marker image 115 which is indicated to protrude upward (in the case of the lower jaw tissue) or downward (in the case of the upper jaw tissue) may be used as an image matching reference with the three-dimensional outer shape image 120.

Also, in the case of the edentulous patient who has no teeth in the mouth, the reference marker image 115 on the three-dimensional image 110 and the reference marker image 125 on the three-dimensional outer shape image 120 may be used as the image matching reference.

Like this, when the distortion occurs on the three-dimensional image 110, or the information for the image matching is insufficient, the reference marker provides a reference point for the image matching. Therefore, the generic technical apparatus which is capable of performing the accurate image matching according to various states in the patient's mouth may be provided.

Also, at least one of the points may be set to a place adjacent to the preset insertion position of the implant. Specifically, the three-dimensional image 110 and the three-dimensional outer shape image 120 may be indicated to be distorted from the actual inner side of the mouth. The distortion may be resolved by the image matching between the three-dimensional image 110 and the three-dimensional outer shape image 120, and a difference between the actual inner side of the mouth and the three-dimensional procedure guide image obtained through the image matching may be minimized.

At this time, since the reference marker as the image matching reference is installed at the place adjacent to the preset insertion position of the implant, the insertion position of the implant and a portion therearound may be more accurately matched and indicated on the three-dimensional procedure guide image. Therefore, in the guide stent manufactured through the three-dimensional procedure guide image, the through-hole guiding the procedure, such as an implant drilling, and a portion therearound may be accurately formed to correspond to the actual inner side of the mouth.

Meanwhile, referring to FIGS. 13 to 15A, the three-dimensional outer shape image 120 may be obtained by the oral scanning. At this time, the oral scanning performed using an oral scanner may be performed in order of a buccal surface (a cheek side), a canine tooth, and a labial surface (a lip side), while the patient's upper and lower teeth are shut, and then performed along a cross-sectional surface of the tooth, while patient's upper and lower teeth are opened.

The scanned image information may be combined in an image information processing device of the oral scanner, and integrated into the three-dimensional outer shape image 120 including an entire shape of the dental crown 122 and the gum 121.

Here, the three-dimensional outer shape image 120 is obtained by combining image information continuously taken by the oral scanner moved along the inner side of the patient's mouth. Therefore, a dental arch 120a on the combined three-dimensional outer shape image 120 may be indicated to be distorted from an actual dental arch a in the mouth.

That is, the dental arch 120a of the three-dimensional outer shape image 120 may have a shape which is wider than a curvature of an actual teeth arrangement in the mouth from anterior teeth toward molar teeth, or bent up and down. The distortion of the dental arch 120a may occur while the scanned images are combined.

At this time, information on a width and a volume of each tooth in the three-dimensional outer shape image 120 accurately indicates information on the actual inner side of the mouth. Therefore, the three-dimensional outer shape image 120 may be corrected with the accurate dental arch, and then combined with the three-dimensional image 110, and thus the three-dimensional procedure guide image which is more accurately matched may be obtained.

Figure 15A:
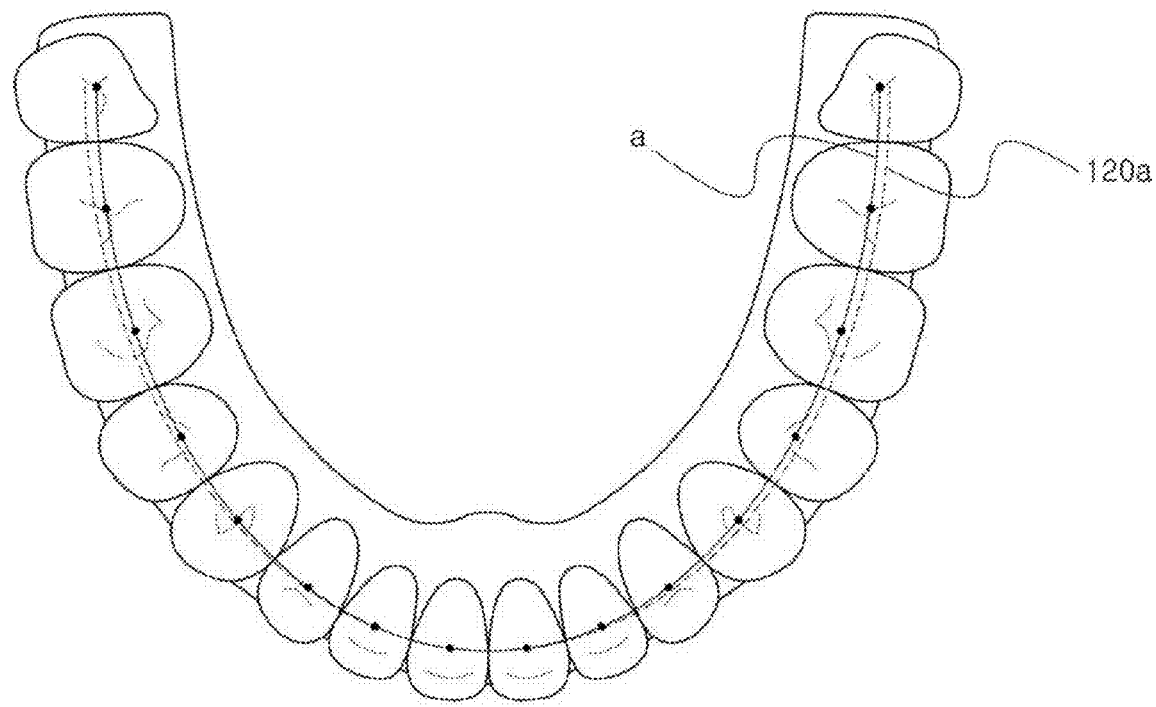
FIGS. 15A and 15B are views illustrating an example of an image matching method in the method of manufacturing the guide stent for implant insertion using the reference marker for attachment in the mouth according to another embodiment of the present invention.
Figure 15B:
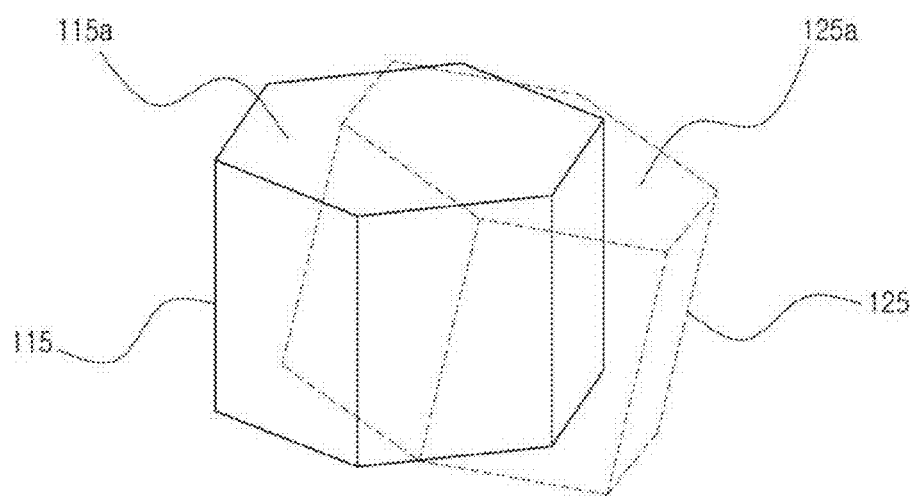

Meanwhile, referring to FIGS. 14 to 15B, an operation s140 of obtaining the three-dimensional procedure guide image may include an operation of correcting the three-dimensional image 110 and the three-dimensional outer shape image 120 so that areas of mutually corresponding portions of matching reference surfaces 115a and 125a, which are calculated to include the matching reference points 116 and 126, coincide with each other.

Here, the matching reference points 116 and 126 are set in the reference marker images 115 and 125 indicated on the three-dimensional image 110 and the three-dimensional outer shape image 120. The matching reference points 116 and 126 may be set at edges of the other surface disposed in parallel with one surface on which the reference marker is adhered to the inner side of the mouth. At this time, the other surface in which the matching reference points 116 and 126 are set may be calculated with the matching reference surfaces 115a and 125a.

The reference marker images 115 and 125 indicated on the three-dimensional image 110 and the three-dimensional outer shape image 120 by the same reference marker may be indicated differently from each other due to a three-dimensional angle of each image, a magnification of each image, and a distortion of the dental arch. At this time, the three-dimensional angle of each image, the magnification of each image, and the dental arch may be converted and corrected by a three-dimensional rendering method using three-dimensional vector information.

Here, the three-dimensional angle and the magnification of each image 110, 120 are corrected so that the areas of the matching reference surfaces 115a and 125a indicated on the three-dimensional image 110 and the three-dimensional outer shape image 120 coincide with each other. Thus, the three-dimensional image 110 and the three-dimensional outer shape image 120 may be matched with each other.

At this time, the three-dimensional outer shape image 120 may be corrected based on the matching reference surface 115a indicated on the three-dimensional image 110 of the three-dimensional image 110 and the three-dimensional outer shape image 120. That is, the three-dimensional angle and the magnification of the three-dimensional outer shape image 120 may be controlled so that the matching reference surface 125a of the three-dimensional outer shape image 120 coincides with the matching reference surface 115a of the three-dimensional image 110.

In a state in which the three-dimensional angle and the magnification of the three-dimensional outer shape image 120 is controlled, the three-dimensional outer shape image 120 included in the difference map 130 is divided into a plurality of vertical cross sections along the dental arch. Then, each vertical cross section of the three-dimensional outer shape image 120 is moved vertically or horizontally so that the matching reference surface 125a of the three-dimensional outer shape image 120 and a dot or a line, by which the matching reference surface 125a is cut, indicated on each cross section coincide with the matching reference surface 115a of the three-dimensional image 110 and a dot or a line, by which the matching reference surface 115a is cut, and thus the dental arch 120a of the three-dimensional outer shape image 120 may be corrected.

Here, an interpolation process which softly connects among cross sections arranged along the dental arch may be performed with the vertical and horizontal movement of the three-dimensional outer shape image 120.

Meanwhile, the operation s140 of obtaining the three-dimensional procedure guide image may include an operation of setting the common portion of the three-dimensional image 110 and the three-dimensional outer shape image 120 as a comparative region, and an operation of correcting an image of the comparative region.

At this time, a region including the reference marker image 115, 125 which is the common portion of each image may be set as the comparative region. Here, a process in which the common portion in each image 110, 120 is calculated, and the comparative region is set may be automatically performed by an image processing device. However, for accuracy of the image matching and enhancement of speed, the operator may manually set the comparative region.

The operation of setting the comparative region may include an operation of decomposing and outputting the matching degree between the images according to colors, and an operation of designating and receiving a portion of the comparative region having the matching degree less than a preset matching degree as an error region.

Here, the matching degree between the three-dimensional image 110 and the three-dimensional outer shape image 120 overlapped in each pixel is indicated in each pixel of the difference map 130, and the matching degree may be indicated by the matching error between the images overlapped in each pixel.

At this time, the difference map 130 indicates the matching error between the images 110 and 120 with colors, and thus the operator may easily recognize the image matching process, and may intuitively determine the accuracy of the image matching result.

For example, referring to a color table 131 for the matching error of FIG. 14, a portion of a surface of the three-dimensional outer shape image 120 which protrudes outside from a surface of the three-dimensional image 110 is indicated with a red color, and a portion of the surface of the three-dimensional outer shape image 120 which is recessed into the surface of the three-dimensional image 110 is indicated with a blue color, and a matched portion therebetween is indicated with a green color.

Therefore, the operator may easily determine whether an important portion in the implant procedure is accurately matched, even after the image matching. If the important portion in the implant procedure is not accurately matched, the image matching operation may be performed again, or the correcting operation may be performed to obtain the more accurately matched image.

The portion having the matching degree the preset matching degree or less means a portion in which a certain matching error occurs, and may be regarded as a portion which has a great influence on the completion of the implant procedure, or a portion having a large error which is difficult to be corrected during the procedure.

Therefore, instead of calculating the entire difference map 130 at a time and correcting the three-dimensional outer shape image 120, the operator manually sets the region having a large error in the difference map 130 through the matching degree decomposed and output by color. Then, the correction is performed in only the set region, and thus an image calculation process may be performed rapidly.

Meanwhile, in one example of the image matching method, the operation of correcting the three-dimensional outer shape image 120 may include an operation of dividing the difference map 130 into the plurality of cross sections along the dental arch within the error region, and an operation of moving the three-dimensional outer shape image 120 up and down and left and right in parallel so that the matching reference surfaces of the images 110 and 120 coincide mutually in each cross section, and thus correcting the dental arch.

At this time, the dental arch means a curve which represents an image of the teeth. For example, when a center point of each tooth is set as a representative point, a U-shaped teeth arrangement curve may be formed along the representative points.

Here, when the information on the dental crown and the gum is restored three-dimensionally based on the dental arch, the three-dimensional outer shape image 120 may be obtained. When the information on the dental crown, the dental root and the alveolar bone is restored three-dimensionally based on the dental arch, the three-dimensional image 110 may be obtained. And when the information on the dental crown, the gum, the dental root and the alveolar bone is restored three-dimensionally based on the aligned dental arch, the three-dimensional procedure guide image may be obtained.

At this time, the representative points may be set at a portion in which the reference marker images 115 and 125 are indicated. The dental arch of the three-dimensional outer shape image 120 is corrected based on the representative points so that the matching reference surfaces 115a and 125a indicated on the cross section of the difference map 130 coincide with each other, and the three-dimensional image 110 and the three-dimensional outer shape image 120 are matched, and thus the three-dimensional procedure guide image may be obtained.

Of course, the above-described image matching method is just an example, and a process of matching different kinds of images using the image matching reference point may be performed in various methods.

Meanwhile, referring to FIG. 2, an operation s150 of manufacturing the stent body 10 according to the obtained three-dimensional procedure guide image may include an operation of forming a matching groove, in which the inner side of the patient's mouth is inserted and fixed, at the stent body 10, and an operation of designing a crown according to the three-dimensional procedure guide image and setting a guide angle of the through-hole 11 for the insertion of the fixture according to a designed arrangement angle of the crown.

Here, the stent body 10 may guide the drilling, while fixed in the patient's mouth. At this time, the gum in the patient's mouth may be inserted and fixed into the matching groove formed at the stent body 10. Then, the through-hole 11 may be formed to accurately guide the positions of the drill and the fixture.

Also, at a time when the three-dimensional procedure guide image is obtained, the crown is substantially simultaneously manufactured with the guide stent 100.

That is, instead of manufacturing the crown to correspond to an installed angle of the fixture, the arrangement angle of the crown may be set and the crown may be manufactured, when the guide stent 100 is manufactured. Therefore, the period of time for preparing the implant procedure and manufacturing various implants may be remarkably reduced. Also, the generic technical apparatus capable of completing the removing of the gum, the drilling of the bore for the insertion of the fixture, the inserting of the fixture and the installing of the abutment/crown with one procedure may be provided.

Figure 16:
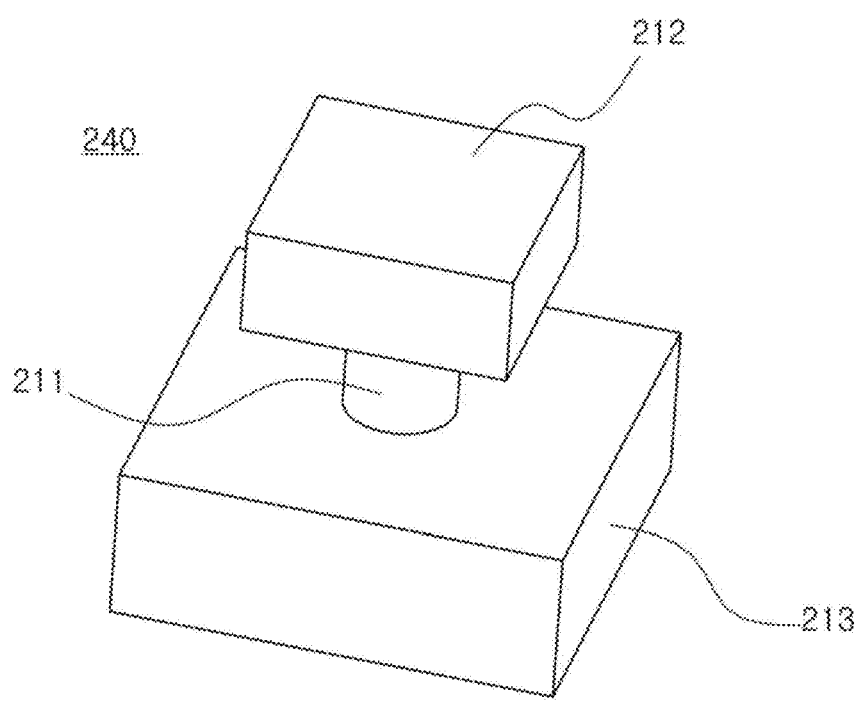
FIGS. 16 and 17 are perspective views illustrating a modified example of the reference marker for attachment in the mouth according to another embodiment of the present invention.

Meanwhile, FIG. 16 illustrates a modified example of the reference marker for attachment in the mouth according to another embodiment of the present invention. Since a basic structure of the embodiment, except a pincette groove 211 formed at a reference marker 240, is the same as that of another embodiment, the repeated description thereof will be omitted.

Referring to FIG. 16, for the image matching, the reference marker 240 for attachment in the mouth is adhered to the inner side of the patient's mouth, and includes an integrated body part 213 indicating the matching reference surface. Here, the body part 213 may be formed in the cylinder or polyprism shape having a certain volume. At this time, an upper surface 212 of the body part 213 may have a square cross section.

Specifically, a lower surface of the body part 213 may be adhered to the inner side of the mouth, and the upper surface 212 thereof may be used as the matching reference surface.

Here, since the upper surface 212 is formed to have the square cross section, an outline thereof may be easily distinguished on the three-dimensional image and the three-dimensional outer shape image. And the upper surface 212 may be provided to be flat, and the image matching process, in which the area of each matching reference surface coincides through the image processing operation, such as horizontal/vertical movement, three-dimensional rotation, and change in magnification, may be smoothly performed.

Also, the lower surface of the body part 213 may be provided wider than the upper surface 212 so as to increase a contact area with the inner side of the mouth, and may be formed in various shapes, such as a circular cross section and a polygonal cross section.

At this time, the body part 213 may be integrally formed by an injection molding, or the like, and may include the pincette groove 211 recessed into one side of an outer circumference of the body part 213. Here, a pincette may be inserted and gripped into an inner side of the pincette groove 211, and thus the reference marker 240 may be caught and fixed by an end of the pincette. Therefore, the reference marker 240 may be prevented from slipping and being fallen, while moved into the patient mouth and then adhered therein.

Figure 17:
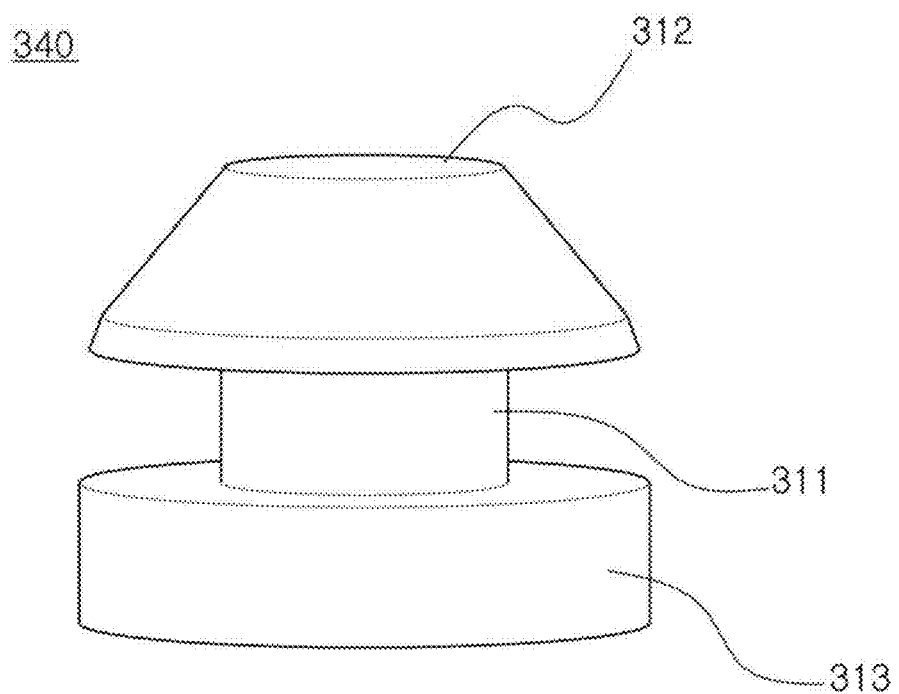

Meanwhile, FIG. 17 illustrates a modified example of the reference marker for attachment in the mouth according to still another embodiment of the present invention.

Referring to FIG. 17, for the image matching, the reference marker 340 includes an integrated body part 313 installed at the inner side of patient's mouth, and a pincette groove 311 may be formed at one side of an outer circumference of the body part 313.

At this time, an upper surface 312 of the body part 313 is formed to have a circular cross section of which an area is gradually reduced toward an upper side thereof. Here, the upper surface 312 may be formed to have a diameter of 4 to 6 mm, preferably, 5 mm.

When the diameter of the upper surface 312 is less than 4 mm, an image of the upper surface 312 used as the matching reference surface may not be clearly distinguished from a side surface of the body part 313 on the three-dimensional image due to limitation of the CT scanner, and thus the image matching result may be inaccurately produced. And when the diameter of the upper surface 312 is more than 6 mm, an image covered by the body part 313 may be increased, and thus the image matching result may be inaccurately produced.

The present invention as described above provides the following effects.

First, the guide stent may automatically align the fixture/abutment so that the crown manufactured according to the three-dimensional procedure guide image is coupled at the preset arrangement angle through the guide protrusion. That is, instead of manufacturing the crown to correspond to the insertion angle of the fixture, the abutment is aligned and coupled at the preset arrangement angle of the crown, when the guide stent is manufactured, and thus after each component is manufactured, a series of procedure processes can be remarkably reduced. Therefore, the generic technical apparatus capable of completing the removing of the gum, the drilling of the bore for the insertion of the fixture, the inserting of the fixture and the installing of the abutment/crown with one procedure can be provided.

Second, when the three-dimensional image and the three-dimensional outer shape image are obtained, even though the image defect is generated by the scattering of light due to the metal implant, a clear image matching reference point can be provided by the reference marker installed in the patient's mouth. Therefore, more accurate image matching results may be obtained corresponding to various states in the patient's mouth.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A dental implant insertion set comprising:
   a fixture configured to be fixed into an alveolar bone and having a hex hole formed therein;
   an abutment including a hex protrusion formed at a lower portion of the abutment and configured to be matched with and fixed in the hex hole, and a guide surface formed at an outer side surface of the abutment to be parallel with one surface of the hex protrusion;
   a crown configured to be aligned with and fixed to the abutment; and
   a guide stent including a stent body configured to be fixed in a patient's mouth and to cover a periodontal tissue in the patient's mouth, coupling hole formed at the stent body, and a sleeve inserted into and fixed in the coupling hole,
   wherein the sleeve has a guide hole formed at an inner circumference of the sleeve to guide an implant drill, and a guide protrusion formed at an outer circumference of the sleeve to guide an insertion angle of the fixture,
   wherein the guide protrusion of the sleeve has a width as the same as a width of the guide surface of the abutment.

2. The dental implant insertion set of claim 1, wherein the guide protrusion is positioned at a preset insertion guide angle and fixed at an edge of the coupling hole to define an alignment position of the fixture.

3. The dental implant insertion set of claim 1,
   wherein the sleeve further includes a groove formed at an outer circumferential surface of the sleeve along a circumferential direction of the sleeve, and a coupling surface formed at the outer circumferential surface of the sleeve and being surface roughness processed in the circumferential direction of the sleeve,
   wherein the groove is configured to be coupled with a protrusion formed at an inner circumferential surface of the coupling hole of the stent body along a circumferential direction of the coupling hole.

4. The dental implant insertion set of claim 1, wherein a coupling groove is formed at the crown so that a coupling protrusion formed at an upper end of the abutment is matched with and fixed in the coupling groove, when the fixture and the abutment are aligned.

5. A method of manufacturing a dental implant insertion set, comprising:
   obtaining a three-dimensional image of periodontal tissue in a patient's mouth through a CT scan and a three-dimensional outer shape image corresponding to the three-dimensional image through an oral scan;
   obtaining a three-dimensional procedure guide image by matching the three-dimensional image and the three-dimensional outer shape image; and
   manufacturing a fixture configured to be fixed into an alveolar bone and having a hex hole, an abutment, a crown having a coupling groove at a lower portion of the crown, and a guide stent,
   wherein the abutment includes a hex protrusion formed at a lower portion of the abutment and configured to be matched with and fixed in the hex hole, a guide surface formed at an outer side surface of the abutment to be parallel with one surface of the hex protrusion, and a coupling protrusion formed at an upper portion of the abutment and configured to be matched with the coupling groove of the crown,
   wherein the guide stent includes a stent body having a coupling hole positioned at a preset insertion position of an implant according to the three-dimensional procedure guide image, and a sleeve having a guide hole formed at an inner circumference of the sleeve to guide an implant drill and a guide protrusion formed at an outer circumference of the sleeve to guide an insertion angle of the fixture,
   wherein the guide protrusion of the sleeve has a width as the same as a width of the guide surface of the abutment.

6. The method of claim 5, further comprising:
   installing a reference marker in a patient's mouth prior to the obtaining the three-dimensional image of periodontal tissue and the three-dimensional outer shape image,
   wherein the obtaining the three-dimensional procedure guide map includes:
   selectively receiving a matching reference point in a reference marker image indicated on the three-dimensional image and the three-dimensional outer shape image; and
   subsequently matching the three-dimensional image and the three-dimensional outer shape image, based on each matching reference point, in a difference map which overlaps the three-dimensional image and the three-dimensional outer shape image and outputs a matching degree therebetween, and thus obtaining the three-dimensional procedure guide image.

7. The method of claim 6, wherein the reference marker is adhered by a resin for provisional attachment of the implant, and installed at three points or more which are spaced from each other in the mouth.

8. The method of claim 7, wherein each of the points is set to at least one of the patient's upper and lower jaw tissues, and set to a position in which another tissue faces at least one of teeth, gum and a roof of the mouth, and
   at least one of the points is set adjacent to a preset insertion position of the implant.

9. The method of claim 6, wherein the subsequently matching the three-dimensional image and the three-dimensional outer shape image comprises converting each image using a three-dimensional rendering method so that areas of corresponding portions of a matching reference surface calculated to include the matching reference points coincide with each other.

* * * * *